(12) United States Patent
Gourlay

(10) Patent No.: US 9,408,959 B2
(45) Date of Patent: Aug. 9, 2016

(54) INTEGRATED PERFUSION DEVICE

(75) Inventor: Terrence Gourlay, Glasgow (GB)

(73) Assignee: University of Strathclyde, Glasgow (GB)

( * ) Notice: Subject to any disclaimer, the term of this patent is extended or adjusted under 35 U.S.C. 154(b) by 506 days.

(21) Appl. No.: 13/811,861

(22) PCT Filed: Jul. 26, 2011

(86) PCT No.: PCT/GB2011/001118
§ 371 (c)(1),
(2), (4) Date: Jun. 10, 2013

(87) PCT Pub. No.: WO2012/013925
PCT Pub. Date: Feb. 2, 2012

(65) Prior Publication Data
US 2013/0280692 A1    Oct. 24, 2013

(30) Foreign Application Priority Data

Jul. 27, 2010   (GB) .................................. 1012521.9

(51) Int. Cl.
*A61M 1/16*    (2006.01)
*A61M 1/32*    (2006.01)
*A61M 1/10*    (2006.01)
*A61M 1/36*    (2006.01)

(52) U.S. Cl.
CPC .............. *A61M 1/32* (2013.01); *A61M 1/1006* (2014.02); *A61M 1/1015* (2014.02); *A61M 1/1036* (2014.02); *A61M 1/1698* (2013.01); *A61M 1/369* (2013.01); *A61M 2205/3673* (2013.01)

(58) Field of Classification Search
CPC ............ A61M 1/1006; A61M 1/1015; A61M 1/1036; A61M 1/1698; A61M 1/32; A61M 1/369; A61M 2205/3673
See application file for complete search history.

(56) References Cited

U.S. PATENT DOCUMENTS 4,306,018 A * 12/1981 Kirkpatrick ....................... 435/2
4,490,331 A    12/1984 Steg, Jr.
(Continued)

FOREIGN PATENT DOCUMENTS

EP    1464350 A1    10/2004
EP    1624912 A2    2/2006
(Continued)

OTHER PUBLICATIONS

Japan Patent Office, Office Action Summary for Application No. 2013-521207, 1 page, Apr. 21, 2015, Japan.
(Continued)

*Primary Examiner* — Philip R Wiest
*Assistant Examiner* — Benjamin Klein
(74) *Attorney, Agent, or Firm* — Alston & Bird LLP

(57) ABSTRACT

An integrated perfusion apparatus or device for use in e.g. extracorporeal membrane oxygenation, cardiopulmonary bypass, or isolated organ or limb perfusion, comprises a blood pump for circulating blood through the device; a blood oxygenator for oxygenating blood, and at least one heat control unit capable of controlling and/or regulating blood temperature within the device, wherein the at least one heat control unit comprises at least one solid state heating and/or cooling source, such as at least one Peltier device. The invention also relates to a method of performing perfusion on a patient, limb or organ, comprising using the perfusion device.

15 Claims, 26 Drawing Sheets

(56) References Cited

U.S. PATENT DOCUMENTS

| | | |
|---|---|---|
| 4,722,829 A | 2/1988 | Giter |
| 5,069,661 A | 12/1991 | Trudell |
| 5,713,730 A | 2/1998 | Nose et al. |
| 6,074,605 A | 6/2000 | Meserol et al. |
| 2003/0097845 A1* | 5/2003 | Saunders et al. .............. 62/3.3 |
| 2004/0079089 A1* | 4/2004 | Wallach .......................... 62/3.2 |
| 2004/0223872 A1 | 11/2004 | Brian et al. |
| 2006/0052854 A1 | 3/2006 | Allers et al. |
| 2007/0276508 A1 | 11/2007 | Fischer et al. |
| 2008/0031773 A1* | 2/2008 | Eccleston .................... 422/44 |
| 2009/0175762 A1 | 7/2009 | Ogihara et al. |

FOREIGN PATENT DOCUMENTS

| | | | |
|---|---|---|---|
| EP | 1930034 A1 | 6/2008 | |
| EP | 1970080 A1 | 9/2008 | |
| JP | S 62691 U | 1/1987 | |
| JP | H 3-131266 A | 6/1991 | |
| JP | 6237992 A | 8/1994 | |
| JP | H 7-116249 A | 5/1995 | |
| JP | H 11502133 A | 2/1999 | |
| JP | 2000005302 A | 1/2000 | |
| JP | 2006296452 A | 11/2006 | |
| JP | 2007-516007 A | 6/2007 | |
| WO | WO96/39817 A1 | 12/1996 | |
| WO | WO97/16213 A2 | 5/1997 | |
| WO | WO 9716213 A2 * | 5/1997 | ............. A61M 1/16 |
| WO | WO97/34647 A1 | 9/1997 | |
| WO | WO99/49913 A1 | 10/1999 | |
| WO | WO00/06357 A1 | 2/2000 | |
| WO | WO00/38818 A1 | 7/2000 | |
| WO | WO01/82999 A2 | 11/2001 | |
| WO | WO2004/043517 A2 | 5/2004 | |
| WO | WO 2005/027578 A1 | 3/2005 | |
| WO | WO2006/031858 A1 | 3/2006 | |

OTHER PUBLICATIONS

International Searching Authority, International Search Rerport and Written Opinion for International Application No. PCT/GB2011/001118, mailed Mar. 23, 2012, 19 pages, European Patent Office, The Netherlands.

Intellectual Property Office, Search Report and Examination Opinion for Application No. GB1012521.9, dated Oct. 5, 2010, 6 pages, United Kingdom.

Intellectual Property Office, Search Report for Claims 6-19, and 28-59 in part for Application No. GB1012521.9, dated Jan. 13, 2011, 3 pages, United Kingdom.

Intellectual Property Office, Search Report for Claims for 20-27 and 28-59 in part for Application No. GB1012521.9, dated Jan. 13, 2011, 3 pages, United Kingdom.

European Patent Office, Communication Persuant to Article 94(3) EPC for Application No. 11745998.2, Dec. 18, 2013, 7 pages, The Netherlands.

Japan Patent Office, Office Action Summary for Application No. 2013-521207, Aug. 25, 2015, 1 page, Japan.

* cited by examiner

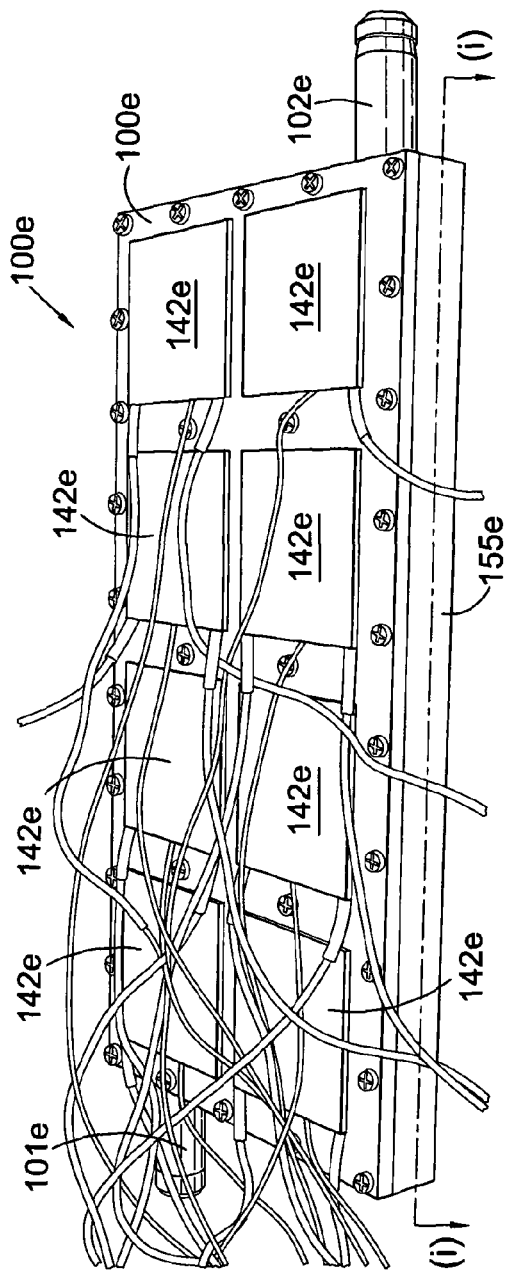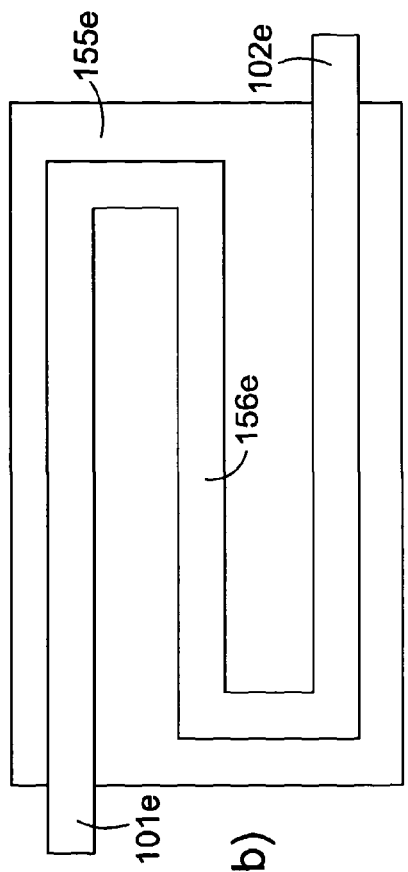
Figure.16(a)
Figure.16(b)

ND PERFUSION DEVICE

INTEGRATED PERFUSION DEVICE

CROSS REFERENCE TO RELATED APPLICATIONS

This application is a National Stage Application, filed under 35 U.S.C. §371, of International Application No. PCT/GB2011/001118, filed Jul. 26, 2011, which claims priority to Great Britain Application No. 1012521.9, filed Jul. 27, 2010, the contents of which is hereby incorporated by reference in its entirety.

BACKGROUND TO THE INVENTION

1. Related Field

The present invention relates to a perfusion device for extracorporeal blood oxygenation procedures, and in particular, though not exclusively, to an integrated perfusion device for use in e.g. extracorporeal membrane oxygenation, isolated organ perfusion, isolated limb perfusion or cardiopulmonary bypass, for example, in a surgical environment.

2. Description of Related Art

Cardiopulmonary Bypass (CPB) is a technique which allows artificial maintenance of the circulation of blood and the oxygen content of the body of a patient, typically undergoing surgery. Therefore, a typical CPB apparatus performs the dual function of mechanically circulating blood and oxygenating blood while bypassing the heart and lungs during a surgical procedure.

Extracorporeal Membrane Oxygenation (ECMO) is a technique employed to support patients who are suffering from, for example, cardiopulmonary distress. ECMO is a simplified form of CPB, and is typically used in applications such as neonatal life support (e.g. for newborns with serious birth defects), or support of recipients for organ transplant.

Typical CPB and ECMO support systems consist of a number of elements which are interconnected to form the overall system. These generally comprise (a) a blood pump; (b) a blood oxygenator; (c) a heat exchanger; (d) connecting tubing; and (e) an arterial or venous reservoir. In addition to the above a number of ancillary devices are required to run these systems in the clinical setting, including a heater/cooler system for providing a cooling/heating fluid to the heat exchanger, typically pumping water through a counter-current heat exchanger positioned in either the arterial or venous lines of the perfusion system.

The heat exchanger is generally used to cool the blood and lower the patient's body temperature during surgery. However, the heat exchanger may also be used to, e.g., maintain normal body temperature, e.g. in neonatal or adult life support, or in isolated organ or limb perfusion. The heat exchanger may also be used to, e.g., heat blood in subjects suffering from hypothermia. Another application of such heat exchangers includes cardioplegic procedures. Cardioplegia, typically employed during open heart surgical procedures, involves stunning the heart by pumping a cooled mixture of blood and cardioplegic solution to the heart, in order to allow surgical procedure to be performed on the heart. The cooled mixture of blood and cardioplegic solution is typically pumped at regular intervals during the procedure. Upon completion of the procedure, the heart is brought back to normothermic temperature by pumping heated blood in a so-called "hot shot".

Such heat exchangers are typically connected to a water circuit which relies on large mains-powered heater/cooler units. The need for a heating/cooling fluid supply and connecting tubes to/from the heat exchanger is not only cumbersome and detrimental to portability, but also presents risks of contamination associated with the presence of blood and water in the same assembly. Further, there exist obvious risks associated with the presence of mains power and water in the same circuit.

Conventional ECMO technologies employ a roller or a centrifugal pump to circulate blood through the circuit. This usually requires that the patient be positioned in an elevated position to ensure gravitation "siphoning" of venous blood into the system. Such excessive patient elevation often complicates clinical care and/or interaction with the patient during deployment.

The use of ECMO is most effectively applied if used aggressively. However, this is often hampered by the availability and complexity of the current technology and is often restricted to specialist units. The complexity of the current ECMO systems, largely involving modified conventional CPB technologies that have large surface areas of foreign materials, also tends to create relatively high blood contacting surfaces in current ECMO systems. This can lead to significant blood/biomaterial contact mediated complications, including activation of inflammatory processes, and consumption of clotting factors. Further, the relatively large priming volumes required during use of the current devices can cause a risk of haemodilution, which may be significant in the neonatal and paediatric setting where haemodilution effects are of real clinical concern.

This complexity and scale also has an impact upon clinical management, for example introducing difficulties in transporting patients for important diagnostic investigations elsewhere within the hospital, contributing significantly to the most challenging medical complications of the procedure.

European Patent Application Publication No. EP 1 624 912 (Cardiovention Inc) discloses an apparatus for oxygenating and pumping blood including a housing defining a blood flow path including, in series, a gas collection plenum, a pump space and a blood oxygenation element. A pump disposed in the pump space is configured to draw blood from the gas collection plenum and propel blood from the pump space through a heat exchanger and the blood oxygenation element. The heat exchanger includes a heat exchange plate and a coolant space.

U.S. Pat. No. 5,069,661 (Brigham and Women's Hospital) discloses a low-pressure, low blood trauma hemodynamic support system. The system may operate as a relatively static-volume, gravity-fed, extracorporeal blood circulation and oxygenation system that consists essentially of (1) a membrane-type blood oxygenator, (2) a non-occlusive roller pump, and (3) connecting tubes.

International Patent Application Publication No. WO 97/34647 (Medtronic, Inc.) discloses waterless temperature control of blood in a blood oxygenator which is achieved by providing a non-disposable heater/cooler with a temperature-controlled surface that can be intimately mated with a heat-conducting surface of a disposable blood heat exchanger associated with the oxygenator.

Japanese Patent No. JP 2006-296452 discloses a pump oxygenator comprising a Peltier unit comprising a Peltier device mounted on several heat exchangers. JP 2006-296452 discloses the use of Peltier devices to maintain temperature in a recirculation circuit. The heat exchangers comprise heat-conducting members in the form of long circular rods extending into the chamber of the heat exchange unit through which a fluid passes.

There is a need in the prior art to improve the portability and compactness of extracorporeal oxygenation devices.

There is a need in the prior art to reduce priming volumes and surface area of foreign materials in contact with blood circulated in extracorporeal oxygenation devices.

There is a need in the prior art to reduce the need for gravity drainage into such systems and provide therapeutic technology closer to the patient.

There is a need in the prior art to eliminate the need for a mains-powered heating/cooling fluid supply (typically a water supply) to control blood temperature and reduce size and improve portability of the overall assembly and mobility of a patient.

It is an object of at least one embodiment of at least one aspect of the present invention to seek to obviate or at least mitigate one or more disadvantages in the prior art.

It is an object of at least one embodiment of at least one aspect of the present invention to provide an integrated perfusion device which minimises priming volumes and surface area of foreign materials in contact with circulated blood.

It is an object of at least one embodiment of at least one aspect of the present invention to provide an integrated perfusion device which reduces the need for gravity drainage into the system.

It is an object of at least one embodiment of at least one aspect of the present invention to provide a portable, compact and integrated perfusion device which eliminates the need for a heating/cooling fluid supply (typically a water supply) to control blood temperature.

BRIEF SUMMARY

According to a first aspect of the present invention there is provided an integrated perfusion apparatus or device comprising a blood pump for circulating blood through the device; and a blood oxygenator for oxygenating blood.

The term "integrated" will be understood to mean that the various components of the device, such as the blood pump and the oxygenator, may form fully integral parts of the device, and that the integrated perfusion device may be used as a single device capable of performing the different functions required during perfusion, e.g. blood circulation, blood oxygenation, and/or blood temperature regulation.

The integrated perfusion device may comprise a heat exchange interface for regulating and controlling blood temperature. By such provision the perfusion device may be capable of regulating and controlling blood temperature as well as oxygenating blood.

The perfusion device may define a blood flow path and/or may comprise at least one blood inlet, at least one blood outlet, at least one ventilating gas inlet for supply to the blood oxygenator, and/or at least one ventilating gas outlet for release of exhausted gas from the blood oxygenator.

The blood flow path may comprise, or may be in contact with, in proximity with, or associated with the heat exchange interface. By such provision the heat exchange interface may permit thermal exchange with blood flowing through the blood flow path.

Preferably, the integrated perfusion device may be a single use integrated perfusion device. By the provision the risks of contamination associated with multi-use surgical devices or parts thereof are eliminated.

The pump may comprise a vortex pump. By such provision, the device may have a very low priming volume and may offer a wide range of operating flow rates.

The pump may comprise an impeller for circulating blood through the perfusion device.

The pump or pump impeller may further comprise a diffuser for diffusing blood into the perfusion device.

The pump impeller may be actuated by e.g. a rotor element, which may be magnetically driven by a magnetic drive system.

The magnetic drive system may comprise bearings, e.g. synthetic diamond bearings, to support the rotor element.

Advantageously, the at least one blood inlet may be provided near the blood pump and/or pump impeller. By such provision the pump may be capable of pumping blood through the at least one blood inlet into the device.

Typically, the at least one blood inlet may be provided radially relative to the pump and/or pump impeller. Alternatively, the at least one blood inlet may be provided axially relative to the pump and/or pump impeller. In another configuration, the at least one blood inlet may be provided, e.g., at an angle relative to the pump and/or pump impeller. It is to be understood that the configuration of the at least one blood inlet relative to the pump and/or pump impeller may be adapted to interact in an optimum manner or complement a particular profile chosen for the pump impeller.

The blood oxygenator may be a counter-current blood oxygenator and may comprise a gas exchange bundle, e.g. a counter-current hollow fibre gas exchange bundle. A counter-current blood oxygenator is understood to refer to an oxygenator in which blood flow and gas flow move in opposite directions.

Typically, when the integrated perfusion device is used in ECMO applications, the blood oxygenator may comprise "plasma-tight" fibres. Plasma-tight fibres are understood in the art to refer to gas exchange fibres which prevent plasma leakage from the high pressure blood phase to the low pressure gas phase when the device is utilised over prolonged periods.

Typically also, when the integrated perfusion device is used in CPB and other applications, the blood oxygenator may comprise "non-plasma-tight" fibres. Non-plasma-tight fibres are understood in the art to refer to gas exchange fibres which are designed for relatively short term use and are not designed to necessarily prevent plasma leakage.

The blood oxygenator may be capable of oxygenating blood processed in the perfusion device.

Advantageously, the blood oxygenator may also be capable of removing at least part, e.g. a predetermined amount, of the carbon dioxide present in the blood to be processed. The carbon dioxide may be released from the blood oxygenator, e.g. through the ventilating gas outlet.

The exhausted gas released through the ventilating gas outlet may be reused, e.g. recirculated, e.g. by a ventilating gas supply or blender for supplying ventilating gas to the oxygenator of the perfusion device. The exhausted gas may be recirculated after treatment of the exhausted gas, e.g. after adjustment of the oxygen and/or carbon dioxide contents in the exhausted gas.

The blood oxygenator may be provided near a central portion of the device, and/or may be, in use, substantially surrounded by the blood flow path. By such provision the contact surface area between the blood and the oxygenator is maximised, and efficiency of oxygenation is optimised.

Typically, the blood oxygenator may be provided at or along at least a portion of the blood flow path between the at least one blood inlet and the at least one blood outlet.

Conveniently, the integrated perfusion device may further comprise at least one blood gate configured to be capable of diverting blood flow within or inside the device so as to bypass the blood oxygenator. The at least one blood gate may be provided along the blood flow path between the at least one blood inlet and the blood oxygenator.

The at least one blood gate may have an open configuration and a closed configuration.

In an open configuration, the at least one blood gate may allow blood flow along the blood flow path between the at least one blood inlet and the at least one blood outlet so as to allow passage through the blood oxygenator.

In a closed configuration, the at least one blood gate may bypass or prevent blood flow through the blood oxygenator.

In such instance, the device may comprise at least one second or bypass blood outlet.

When the blood gate is in a closed configuration, the blood flow path may be provided between the at least one blood inlet and the at least one second or bypass blood outlet.

By such provision the device may act as a blood circulation device or Ventricular Assist Device (VAD). In a clinical environment, this may allow a user, e.g. a clinician, to assess functionality of the lungs of a patient while maintaining blood circulation support.

In a first embodiment of the invention, the integrated perfusion device may further comprise at least one heat control unit capable of controlling and/or regulating blood temperature.

Conveniently, the at least one heat control unit may comprise the heat exchange interface.

Preferably, the heat control unit may comprise at least one heating and/or cooling source.

Advantageously, the at least one heating and/or cooling source may comprise a solid state heating and/or cooling source. By such provision the need for a heating/cooling fluid supply, e.g. a water supply, to control blood temperature may be eliminated. Further, the solid state heating and/or cooling source may be integrated into the perfusion device thus reducing size of the device.

The at least one heating and/or cooling source may be capable of heating and/or cooling, preferably capable of both heating and cooling.

The at least one heating and/or cooling source may comprise a Peltier device. A Peltier device is understood in the art to be a type of solid-state thermoelectric heat pump which transfers heat with consumption of electrical energy. By such provision reliable, rapid temperature control may be achieved. Further, Peltier devices are relatively inexpensive and may be suitable for use in a single use perfusion device.

The at least one heating and/or cooling source may be capable of regulating blood temperature in the range of 10-40° C., preferably the range of 18-38° C.

Typically, the heat exchange interface may comprise at least one heat exchanger which may be in contact with or connected to the at least one heating and/or cooling source of the heat control unit.

Typically, a first side or portion of the at least one heat exchanger may be in contact or in proximity with the fluid to be heated/cooled, e.g. blood.

Advantageously, the first side or portion of the at least one heat exchanger may be provided at or near at least a portion the blood flow path between the at least one blood inlet and the at least one blood outlet and/or the at least one bypass blood outlet.

In one embodiment, the blood flow path may comprise or may be in contact with, in proximity with, or associated with substantially the whole or part of the first side or portion of the at least one heat exchanger.

In an alternative embodiment, the blood flow path may comprise a conduit extending at least partially in contact or in proximity with the first side or portion of the at least one heat exchanger. The blood flow path may have a convoluted or tortuous configuration and/or may extend so as to maximise a length/area of thermal exchange with the first side or portion of the at least one heat exchanger.

A second or opposite side of the at least one heat exchanger may be in contact with one or more of the at least one heating and/or cooling source.

The heat control unit may further comprise at least one thermo-conductive portion, e.g. a thermo-conductive gel, which may be provided between the second side of one or more of the at least one heat exchanger and one or more of the at least one heating and/or cooling source. By such provision heat transfer performance may be further optimised.

Typically, the at least one heat exchanger may be made of a thermoconductive material, e.g. a metal such as aluminium, or a synthetic material such as a polymeric material or a metal/polymer composite material.

The at least one heating and/or cooling source may be provided on an external portion of the perfusion device, e.g. on an external wall of the device.

The at least one heat exchanger may be provided on or form at least part of an external portion of the perfusion device, e.g. of wall of the device such as an external wall thereof. In one embodiment, a plurality of heat exchangers may be disposed within an external portion of the perfusion device, e.g. within wall of the device such as an external wall thereof. In an alternative embodiment, a heat exchanger may form a substantial part of an external portion of the perfusion device, e.g. of wall of the device such as an external wall thereof. By such provision the device may permit effective thermal exchange with the fluid without the disadvantage of interfering with the fluid flow path. Such interference to maximise heat exchange, e.g. through protrusions into the fluid flow path, is undesirable in the context of clinical applications as it increases the risk of unhygienic contamination, and also increases the risk of haemolysis due to increased turbulence in the blood flow. Therefore, the present configuration may act to improve safety and/or hygiene of the integrated perfusion device.

Preferably the at least one heat exchanger does not extend into or does not physically interfere with the fluid flow path.

Advantageously, the at least one heating and/or cooling source may be battery powered. By such provision the need for mains power supply to control blood temperate may be eliminated.

Advantageously, the integrated perfusion device and/or the heat control unit may comprise a plurality of solid state heating and/or cooling sources such as Peltier elements. By such provision blood temperature may be regulated and/or controlled rapidly and accurately. Further, failure of one or several of the plurality of solid state heating and/or cooling sources may not compromise the performance of the device as the remaining solid state heating and/or cooling source(s) may be capable of regulating and controlling blood temperature. Thus, safety of a patient may be improved.

The integrated perfusion device may comprise 2-10, preferably 4-8, typically approximately 6 to 8 solid state heating and/or cooling sources.

The heat control unit may further comprise a temperature control unit.

The temperature control unit may be configured for monitoring and/or controlling the temperature of the heat control unit, e.g. of the at least one solid state heating and/or cooling source.

The temperature control unit may monitor and/or control the overall temperature of the heat control unit, e.g. of the at least one solid state heating and/or cooling source, e.g. an average temperature of the at least one solid state heating and/or cooling source. Advantageously, the temperature control unit may monitor and/or control, e.g. preferably independently, the temperature of each of the at least one solid state heating and/or cooling source. By such provision, the temperature of the heat control unit may be regulated not only based on an average or overall temperature, but also based on the temperature of each individual solid state heating and/or cooling source, thus improving performance and safety.

The temperature control unit may monitor and/or control the temperature of each of the at least one solid state heating and/or cooling source in a cyclic manner.

The temperature control unit may be automated, e.g. may comprise a computer.

The temperature control unit may comprise a shut-down or override function, e.g. may be capable of shutting down or overriding the at least one solid state heating and/or cooling source, preferably independently each of the at least one solid state heating and/or cooling source. By such provision, one or more of the solid state heating and/or cooling sources may be shut down in case of malfunction without compromising performance of the heat control unit, thus improving safety to a patient.

In a second embodiment of the invention, the heat exchange interface may comprise at least part of the blood oxygenator. In such instance, temperature control may be performed by controlling the temperature of the ventilating gas supplied to the oxygenator. Thus, the integrated perfusion device may be devoid of a separate heat control unit.

The gas exchange bundle of the blood oxygenator may comprise the heat exchange interface.

Temperature control of the ventilating gas may be carried out through a gas heat exchanger.

The gas heat exchanger may comprise a solid state gas heat exchanger. The solid state gas heat exchanger may comprise a gas expansion chamber which may be heated by, for example, a heat wrap device.

The gas heat exchanger may comprise a solid state gas heat exchanger. The solid state gas heat exchanger may comprise a gas expansion chamber which may be heated by, for example, a heat wrap device.

Alternatively, gas heat exchanger may comprise a water bath. The water bath may comprise a heated or refrigerated tank, e.g. a heated or refrigerated water tank. A gas conduit, e.g., copper tubing, may pass through or may be immersed in the heated or refrigerated tank. Thus, flow of ventilating gas through gas conduit may allow the ventilating gas to be heated or cooled prior to delivery to the oxygenator of the perfusion device.

The gas heat exchanger may be provided near or upstream from the at least one gas inlet.

The integrated perfusion may further comprise a gas heat control unit which may be capable of controlling temperature of the ventilating gas.

The integrated perfusion device may further comprise at least one oxygen sensor for measuring venous and/or arterial oxygen levels.

The at least one oxygen sensor may comprise a colorimetric sensor which may be positioned at or near the at least one blood inlet and/or the at least one blood outlet and/or the at least one bypass blood outlet of the device.

The integrated perfusion device may further comprise at least one outlet blood flow sensor.

The at least one outlet blood flow sensor may be positioned at or near the at least one blood outlet and/or the at least one bypass blood outlet of the device.

The at least one outlet blood flow sensor may comprise, e.g. at least one ultrasonic Doppler blood flow sensor, and may be attached, e.g. clipped, to an outlet conduit, e.g. an outlet tube, and may optionally interface with the outlet conduit through an acoustic gel.

The integrated perfusion device may further comprise at least one inlet blood flow sensor.

The at least one inlet blood flow sensor may be positioned at or near the at least one blood inlet of the device.

The at least one inlet blood flow sensor may comprise, e.g. at least one ultrasonic Doppler blood flow sensor, and may be attached, e.g. clipped, to an inlet conduit, e.g. an inlet tube, and may optionally interface with the inlet conduit through an acoustic gel.

The integrated perfusion device may further comprise at least one bubble detector, e.g. at least one ultrasonic bubble detector, to detect possible flow of air into the blood flow path. By such provision potential risk of air embolus to, e.g. a patient, is reduced.

The at least one bubble detector may comprise a Doppler bubble detector.

In one embodiment, the at least one bubble detector may be incorporated into the at least one inlet or outlet blood flow sensor.

In an alternative embodiment, the at least one bubble detector may be attached, e.g. clipped, to an inlet conduit, e.g. an inlet tube, or to an outlet conduit, e.g. an outlet tube, and may optionally interface with the inlet or outlet conduit through an acoustic gel.

The integrated perfusion device may further comprise a control unit which may control or interact with the blood pump so as to be capable of regulating the inlet and/or the outlet blood flow.

The control unit may comprise a user interface which may display, e.g. outlet blood flow rate, inlet blood flow rate, venous and/or arterial oxygen levels, and/or air bubble levels.

The user interface may comprise a screen, e.g. an LCD touchpad screen.

The user interface and/or control unit may be connected to the perfusion device, e.g. via an optionally adjustable arm.

Conveniently, the control unit may be in communication with the at least one outlet blood flow sensor and/or the at least one inlet blood flow sensor.

The control unit may comprise an automated mode in which the control unit may automatically control and/or adjust the blood pump flow rate when the inlet and/or outlet blood flow is outside a predetermined range.

In the automated mode, the control unit may automatically control and/or adjust the ventilating gas inlet flow rate, and/or the oxygen ratio of a ventilating gas supply or blender connected to the ventilating gas inlet, when the venous and/or arterial oxygen levels are outside a predetermined range.

By providing an automated mode, the device may be suitable for use in non-specialist ECMO or CPB centres, and/or by non-specialist personnel.

Alternatively, or additionally, the control unit may comprise a manual mode in which a user may manually control and/or adjust the blood pump flow rate, e.g. though the user interface, when the inlet and/or outlet blood flow is outside a range of predetermined flow rates.

In the manual mode, the control unit may allow a user to manually control and/or adjust, e.g. though the user interface, the ventilating gas inlet flow rate, and/or the oxygen ratio of a gas ventilating gas blender connected to the ventilating gas inlet, when the venous and/or arterial oxygen levels are outside a predetermined range.

The control unit may also allow a user to operate the blood flow gate.

Conveniently, the control unit and/or the user interface may further comprise an alarm and/or warning display, e.g. visual or sound display, which may be in communication with, e.g. the at least one oxygen sensor, the at least one bubble detector, and or the at least one outlet and/or inlet blood flow sensor.

The at least one oxygen sensor may trigger activation of the alarm and/or warning display when the at least one oxygen sensor detects that venous and/or arterial oxygen levels are outside a predetermined range.

The at least one bubble detector may trigger activation of the alarm and/or warning display when the at least one at least one bubble detector detects that air bubble levels in the blood flow are above a predetermined level.

The at least one at least one outlet and/or inlet blood flow sensor may trigger activation of the alarm and/or warning display when the at least one outlet and/or inlet blood flow sensor detects that outlet and/or inlet blood flow rate are outside a predetermined range.

Conveniently, the control unit may be remotely accessible by Bluetooth™ technology, WiFi technology and the like. By such provision a user may be able to control and/or operate the control unit remotely.

Alternatively, the at least one oxygen sensor for measuring venous and/or arterial oxygen levels, at least one outlet blood flow sensor, at least one inlet blood flow sensor, at least one bubble detector, and/or at least one control unit may be provided on or within a housing which may be configured for receiving the integrated perfusion device.

By such provision the perfusion device may be described as a 'cartridge'-type device which may be inserted into the housing.

The perfusion device may be kept, e.g. stored, in a sterile environment, e.g. in a sealed sterile container, before use. By such provision use of the perfusion device reduces the risks of contamination of a patient as compared to conventional perfusion systems. Further, the perfusion device may be discarded or disposed of after use. Thus the perfusion device may be termed a single-use or disposable device.

The housing may comprise retention means, e.g. one or more slots, for receiving and/or holding the perfusion device within the housing.

The perfusion device may comprise holding means, e.g. one or more ridges, for engaging with the retention means of the housing.

Conveniently, the retention means of the housing and the holding means of the perfusion device may be complementary and/or may inter-engage with each other.

The housing and/or perfusion device may further comprise attaching means, e.g. clips, bolts or the like, for securing the perfusion device to the housing.

According to a second aspect of the present invention there is provided a casing for use in the device according to the first aspect, the casing defining a blood flow path and comprising at least one blood inlet, at least one blood outlet, at least one ventilating gas inlet, and at least one ventilating gas outlet.

Preferably, the casing may be a single use or disposable casing.

Typically, the casing may comprise a pump receiving portion configured to receive a blood pump, e.g. a vortex blood pump.

Typically also, the casing may comprise an oxygenator receiving portion configured to receive a blood oxygenator.

Alternatively, the blood oxygenator may form part of the casing itself, e.g. be formed integrally with the casing.

The blood oxygenator may be provided near a central portion of the casing, and/or may be, in use, substantially surrounded by the blood flow path.

The casing may further comprise at least one blood gate receiving portion arranged to receive at least one blood gate configured to be capable of diverting blood flow within or inside the device so as to bypass the blood oxygenator.

Alternatively, the at least one blood gate may form part of the casing itself, e.g. may be formed integrally with the casing.

The casing may comprise at least one second or bypass blood outlet to allow blood outflow when the at least one blood gate is in a closed configuration.

The casing may comprise an integral casing unit. Alternatively, the casing may comprise a plurality of connectable, e.g. sealably connectable, portions, e.g. a base portion, a top portion, and at least one central portion provided between the base portion and the top portion.

Typically, the at least one blood inlet may be connected to a venous blood vessel of e.g. a patient, limb or organ, by e.g. a blood inlet conduit or tube.

Typically, the at least one blood outlet and/or the at least one bypass blood outlet may be connected to an arterial blood vessel of e.g. a patient, limb or organ, by e.g. a blood outlet conduit or tube.

The at least one ventilating gas inlet may be connected to a source of ventilating gas for supply to the blood oxygenator, by e.g. a gas inlet conduit or tube.

The at least one ventilating gas outlet may be connected to e.g. a source of ventilating gas, a gas treatment unit, or a gas disposal unit for release of exhausted gas from the blood oxygenator, by e.g. a gas outlet conduit or tube.

A width and/or height of the casing may be in the range of approximately 5-50 cm, and typically in the range of approximately 10-30 cm.

In a first embodiment of the second aspect of the invention, the casing may further comprise at least one heat control unit capable of controlling and/or regulating the temperature of blood circulating through the blood flow path.

Alternatively, the casing may comprise at least one receiving portion for receiving the at least one heat control unit.

Preferred features of the at least one heat control unit are described in relation to the first aspect of the invention, and are not repeated here for brevity.

The at least one heating and/or cooling source of the at least one heat control unit may be provided on an external portion of the casing, e.g. on an external wall of the casing.

The at least one heat exchanger of the at least one heat control unit may be provided on or form at least part of an external portion of the casing, e.g. of an external wall of the casing. In one embodiment, a plurality of heat exchangers may be disposed within an external portion of the casing, e.g. within an external wall of the casing. In an alternative embodiment, the at least one heat exchanger may form a substantial part of an external portion of the casing, e.g. of an external wall of at least one side of the casing.

Advantageously, the at least one heating and/or cooling source may be battery powered.

Advantageously, the casing may comprise a plurality of solid state heating and/or cooling sources.

The casing may comprise 2-10, preferably 4-8, typically approximately 8 solid state heating and/or cooling sources.

In a second embodiment of the second aspect of the invention, the casing may be devoid of a heat control unit and/or of a heat control unit receiving portion. In such instance temperature control may be performed by controlling the temperature of the ventilating gas supplied to the oxygenator.

Temperature control of the ventilating gas may be carried out through a gas expansion chamber which may be heated by a heat wrap device.

Alternatively, the casing may further comprise a receiving portion for receiving a gas heat control unit which may be capable of controlling temperature of the ventilating gas.

The casing according to the first or the second embodiment of the second aspect of the invention may further comprise a control unit receiving portion for receiving a control unit.

Alternatively, the control unit may be attached or connected to the casing by conventional means, e.g. via an optionally adjustable arm.

The features associated with the control unit are described in relation to the first aspect of the present invention and are not repeated here for brevity.

According to a third aspect of the present invention there is provided a pump for use in a device according to the first aspect or a casing according to the second aspect of the invention.

The pump may comprise a vortex pump. By such provision, the device may have a very low priming volume and may offer a wide range of operating flow rates.

The pump may comprise an impeller for circulating blood through the perfusion device.

The pump or pump impeller may further comprise a diffuser for diffusing blood into the perfusion device.

The pump impeller may be actuated by e.g. a rotor element, which may be magnetically driven by a magnetic drive system.

The magnetic drive system may comprise bearings, e.g. synthetic diamond bearings, to support the rotor element.

According to a fourth aspect of the present invention there is provided a perfusion assembly comprising a device according to the first aspect of the present invention.

The term "assembly" will be herein understood to refer to an apparatus comprising said device according to the present invention, and any additional or peripheral equipment, parts or devices which are necessary or advantageous in the performance of a particular clinical or surgical procedure, including for example tubing, controllers, detectors, sensors, regulators, meters, or reservoirs.

The perfusion assembly may comprise a housing configured for receiving the integrated perfusion device.

By such provision the perfusion device may be described as a 'cartridge'-type device which may be inserted into the housing.

The perfusion device may be kept, e.g. stored, in a sterile environment, e.g. in a sealed sterile container, before use. By such provision use of the perfusion device reduces the risks of contamination of a patient as compared to conventional perfusion systems. Further, the perfusion device may be discarded or disposed of after use. Thus the perfusion device may be termed a single-use or disposable device.

The housing may comprise retention means, e.g. one or more slots, for receiving and/or holding the perfusion device within the housing.

The perfusion device may comprise holding means, e.g. one or more ridges, for engaging with the retention means of the housing.

Conveniently, the retention means of the housing and the holding means of the perfusion device may be complementary and/or may inter-engage with each other.

The housing and/or perfusion device may further comprise attaching means, e.g. clips, bolts or the like, for securing the perfusion device to the housing.

The at least one oxygen sensor for measuring venous and/or arterial oxygen levels, at least one outlet blood flow sensor, at least one inlet blood flow sensor, at least one bubble detector, and/or at least one control unit may be provided on or within the housing.

The housing may be of such a size as being capable of receiving the perfusion device.

A width and/or height of the housing may be in the range of approximately 5-50 cm, and typically in the range of approximately 10-30 cm.

The size of the perfusion device may vary depending on the application envisaged. For example, the size of the pump and/or oxygenator and/or optionally heat exchange interface may be relatively large for application in adult perfusion, whereas the size of the pump and/or oxygenator and/or optionally heat exchange interface may be smaller for use in infant/child perfusion.

Conveniently, the perfusion device may comprise a casing according to the second aspect of standard size, e.g. suitable for and/or complementary with the housing of the perfusion assembly, Conveniently also, the size of the pump and/or oxygenator and/or optionally heat exchange interface may be of a first or large size when intended for use in e.g. adult perfusion, and of a second or small size when intended for use in e.g. infant/child perfusion. It will be appreciated that other sizes, e.g. intermediate sizes, maybe envisaged for e.g. intermediate children age groups.

The perfusion assembly, e.g. the housing of the perfusion assembly, may comprise actuating means, e.g. a rotor element, for driving, e.g. magnetically driving, a portion, e.g. the impeller, of the pump.

The actuating means, e.g. the rotor element, may be magnetically driven by a magnetic drive system.

The magnetic drive system may comprise bearings, e.g. synthetic diamond bearings, to support the rotor element.

The perfusion assembly may further comprise an inlet conduit, e.g. an inlet tube, for carrying blood from, e.g. a patient, limb or organ, to the at least one inlet of the perfusion device.

The perfusion assembly may further comprise an outlet conduit, e.g. an outlet tube, for carrying blood from the at least one outlet and/or the at least one bypass blood outlet the perfusion device to, e.g. a patient, limb or organ.

The perfusion assembly may further comprise a ventilating gas supply or blender for supplying ventilating gas to the oxygenator of the perfusion device.

The perfusion assembly may further comprise a gas inlet conduit, e.g. a gas inlet tube, for supplying ventilating gas from the ventilating gas supply or blender to the at least one ventilating gas inlet of the perfusion device.

The perfusion assembly may further comprise a gas outlet conduit, e.g. a gas outlet tube, for carrying exhausted gas from the ventilating gas outlet of the perfusion device to the ventilating gas supply or blender or to a gas treatment unit or waste.

The perfusion assembly may further comprise at least one reservoir for injecting one or more substances into the blood flow.

Typically, the at least one reservoir may comprise e.g. fluids and/or an anticoagulant substance such as heparin.

In a first embodiment, the perfusion assembly may comprise a perfusion device according to the first embodiment of the first aspect of the present invention.

In a second embodiment, the perfusion assembly may comprise a perfusion device according to the second embodiment of the first aspect of the present invention.

In the second embodiment, the perfusion assembly may further comprise means for controlling the temperature of the ventilating gas.

The means for controlling the temperature of the ventilating gas may comprise e.g. a gas expansion chamber which may be heated by e.g. a heat wrap device.

Alternatively, the means for controlling the temperature of the ventilating gas may comprise a gas heat control unit which may optionally be connected to or provided within the perfusion device according to the second embodiment of the first aspect of the present invention.

The perfusion assembly may further comprise at least one oxygen sensor for measuring venous and/or arterial oxygen levels, at least one outlet blood flow sensor, at least one inlet blood flow sensor, at least one bubble detector, and/or at least one control unit. The features of these parts are described in relation to the first aspect of the invention and are therefore not repeated here for brevity.

The at least one oxygen sensor for measuring venous and/or arterial oxygen levels, at least one outlet blood flow sensor, at least one inlet blood flow sensor, at least one bubble detector, and/or at least one control unit may be provided, e.g., within the housing of the perfusion assembly.

The perfusion assembly may comprise an ECMO assembly.

Alternatively, the perfusion assembly may comprise a CPB assembly.

Alternatively, the perfusion assembly may comprise an isolated limb perfusion assembly, e.g. for cancer therapy.

Alternatively, the perfusion assembly may comprise an isolated organ perfusion assembly, e.g. for transplantation and/or treatment.

Alternatively, the perfusion assembly may comprise a limb preservation assembly, e.g. for military field application in the treatment of ballistic injuries.

Alternatively, the perfusion assembly may comprise a neurosurgery assembly.

Alternatively, the perfusion assembly may comprise a liver surgery or a pancreatic surgery assembly.

Alternatively, the perfusion assembly may comprise a vascular assembly.

According to a fifth aspect of the present invention there is provided a method of performing perfusion on a patient, limb or organ, comprising using a perfusion device according to the first aspect, or a perfusion assembly according to the fourth aspect.

In a first embodiment, the method may comprise controlling and/or regulating blood temperature by use of at least one heat control unit which may comprise at least one heating and/or cooling source, e.g. at least one solid state heating and/or cooling source.

In a second embodiment, the method may comprise controlling and/or regulating blood temperature by controlling the temperature of the ventilating gas supplied to the oxygenator.

The method may be for use in ECMO, CPB, isolated limb perfusion, e.g. cancer therapy, isolated organ perfusion, e.g. for transplantation and/or treatment of an isolated organ, limb preservation, e.g. for military field application in the treatment of ballistic injuries, neurosurgery, liver surgery or pancreatic surgery, and/or vascular procedures.

According to a sixth aspect of the present invention there is provided an apparatus or device comprising a blood pump for circulating blood; and at least one heat control unit capable of controlling and/or regulating blood temperature.

The apparatus or device may comprise a cardioplegic apparatus or device.

The blood pump may be configured for circulating blood to the heart of a patient.

Typically, the blood pump may comprise a roller pump.

Typically, the roller pump may be provided between the pump and the heart of a patient.

The apparatus or device may comprise an integrated apparatus or device. The term "integrated" will be understood to mean that the various components of the device, such as the blood pump and the at least one heat control unit, may form fully integral parts of the device, and that the integrated device may be used as a single device capable of performing the different functions required during use, such as during cardioplegia, e.g. blood circulation and/or blood temperature regulation.

The at least one heat control unit may comprise at least one heating and/or cooling source, preferably at least one solid state heating and/or cooling source. By such provision the need for a heating/cooling fluid supply, e.g. a heated/cooled water bath, to control blood temperature may be eliminated.

The at least one solid state heating and/or cooling source may comprise a Peltier device.

The at least one heat control unit may comprise a heat exchange interface and/or at least one heat exchanger which may be in contact with, in proximity with, or associated with the at least one heating and/or cooling source of the heat control unit.

The features of the heat control unit, heat exchange interface, and/or heat exchanger described in respect of the first aspect of the present invention may apply to the heat control unit, heat exchange interface, and/or heat exchanger of the apparatus or device according to the sixth aspect of the present invention, are and therefore not repeated here for brevity.

According to a seventh aspect of the present invention there is provided an assembly comprising a device according to the fifth aspect of the present invention.

The assembly may comprise a cardioplegic assembly.

The assembly may further comprise at least one reservoir for supplying one or more substances, e.g. a cardioplegic solution, into the blood flow, e.g. via the blood pump.

According to an eighth aspect of the present invention there is provided a method of performing cardioplegia on a patient, comprising using a cardioplegic device according to the sixth aspect, or a cardioplegic assembly according to the seventh aspect.

BRIEF DESCRIPTION OF THE FIGURES

Embodiments of the invention will now be given by way of example only, and with reference to the accompanying drawings, which are:

FIG. 11b a top view of the water bath of the gas heat exchanger of the assembly of FIG. 11a;

FIG. 12b a graph showing the air temperature difference (outlet-inlet) across the oxygenator used in the assemblies of FIGS. 10 and 11a;

FIG. 12c a graph showing the water temperature difference (outlet-inlet) across the oxygenator used in the assemblies of FIGS. 10 and 11a;

FIG. 16(a) an elevated front view of an embodiment of an integrated perfusion device according the invention;

FIG. 16(b) a cross-sectional view along a line (i)-(i) of the device of FIG. 16(a);

DETAILED DESCRIPTION OF VARIOUS EMBODIMENTS

Figure 1:
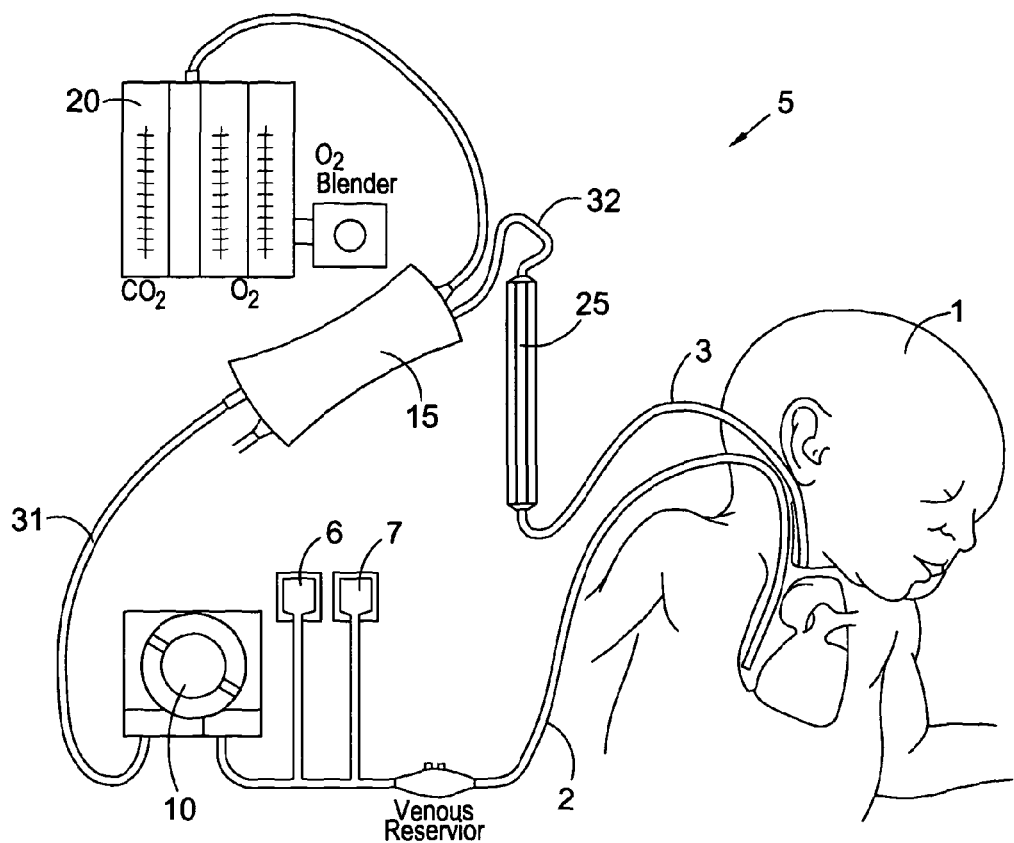
FIG. 1 a conventional ECMO assembly according to the prior art.

Referring to FIG. 1 there is shown a conventional ECMO assembly, generally designated 5, according to the prior art.

The assembly 5 comprises a pump 10 for circulating the blood of a patient 1 through the assembly 5.

The assembly is connected at one end to a venous system of the patient 1 via a venous cannula 2, and at the other end to an arterial system of the patient 1 via an arterial cannula 3. Blood is drawn from the venous cannula 2, circulated through the assembly 5 for oxygenation, and back into the patient via the arterial cannula 3.

The assembly 5 comprises a reservoir of fluids 6 and heparin 7 for treating the patient's blood.

The assembly also comprises a membrane oxygenator 15 which is connected to a gas blender 20 which supplies the oxygenator 15 with ventilating gas for oxygenation of blood through the oxygenator 15.

Blood then passes through a heat exchanger 25 to maintain blood at a predetermined temperature before feeding the oxygenated blood back into the patient 1.

This particular ECMO assembly also comprises a pre-membrane pressure monitor 31 and a post-membrane pressure monitor 32 for measuring blood pressure respectively before and after oxygenation.

The heat exchanger 25 is conventionally connected to a heater/cooler unit (not shown), typically a mains-powered water heating/cooling unit.

This typical type of ECMO assembly illustrates the complexity of such an assembly, and the challenges involved in trying to miniaturise and simplify such an assembly.

Referring to FIGS. 2(a), 2(b), 2(c), 3(a), 3(b) and 3(c) there is shown an integrated perfusion device, generally designated 100, according to a first embodiment of a first aspect of the present invention.

The integrated perfusion device 100 comprises a blood pump 110 for circulating blood through the device 100; a blood oxygenator 120 for oxygenating blood.

In this embodiment, the integrated perfusion device comprises a heat exchange interface 130 for regulating and controlling blood temperature.

The perfusion device 100 defines a blood flow path and comprises a blood inlet 101, a blood outlet 102, a ventilating gas inlet 121 for supply to the blood oxygenator 120, and a ventilating gas outlet 122 for release of exhausted gas from the blood oxygenator 120.

Preferably, the integrated perfusion device 100 is a single use or disposable integrated perfusion device. By the provision the risks of contamination associated with multi-use surgical devices or parts thereof are eliminated.

The pump 110 comprises a vortex pump 111, which comprises an impeller 112 for circulating blood through the perfusion device 100.

The pump 110 further comprises a diffuser 114 connected to the impeller 112 for diffusing blood into the perfusion device 100.

The impeller 112 of the pump 110 is actuated by a rotor element (not shown). In this embodiment, the rotor element is magnetically driven by a magnetic drive system 113.

In one embodiment, the magnetic drive system 113 comprises bearings, e.g. synthetic diamond bearings, to support the rotor element.

The blood inlet 101 is provided near the blood pump 110. By such provision the pump 110 is capable of pumping blood through the blood inlet 101 into the device 100.

Figure 2A:
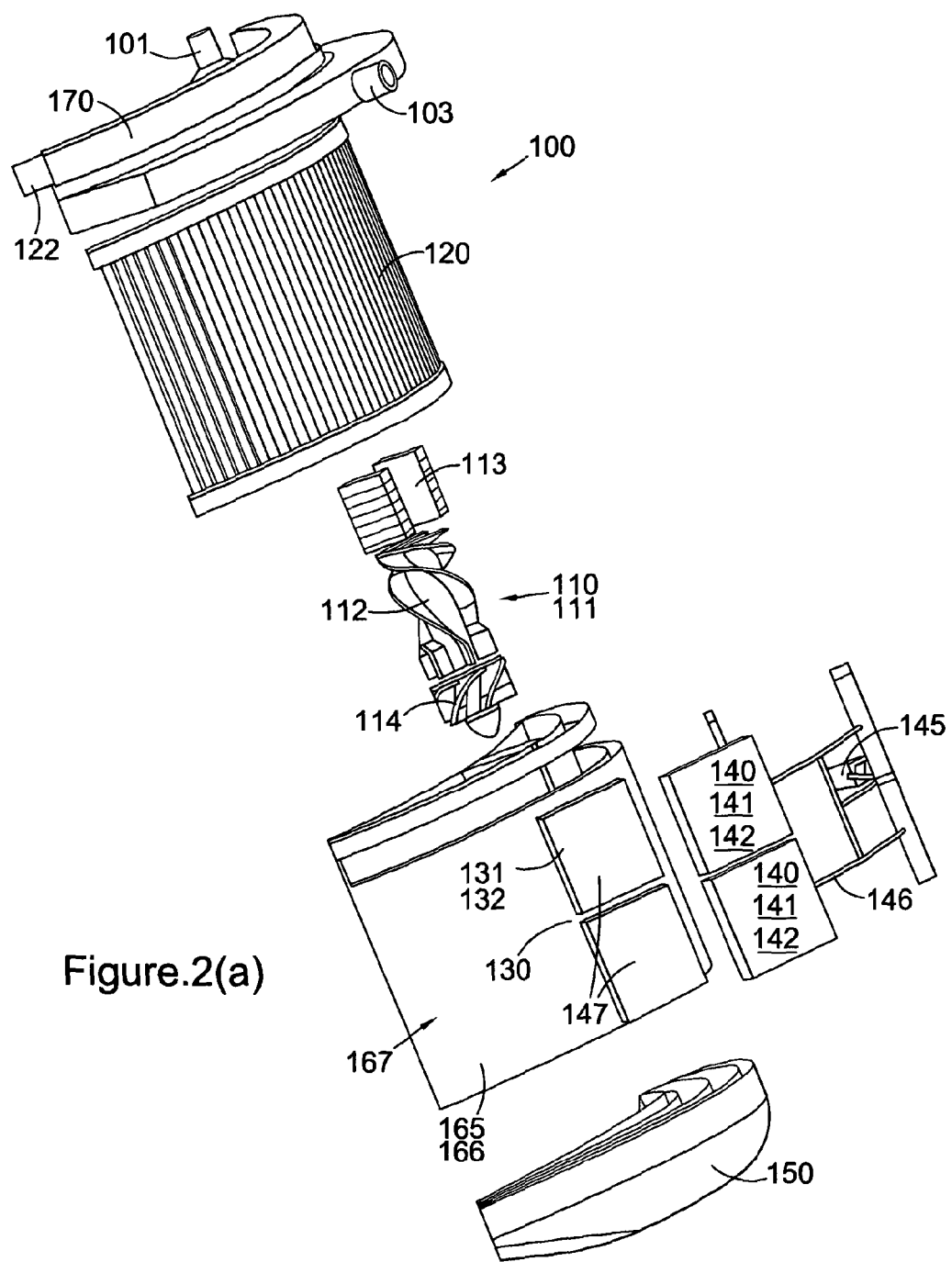
FIG. 2(a) an exploded view of an integrated perfusion device according to a first embodiment of a first aspect of the present invention.
Figure 2B:
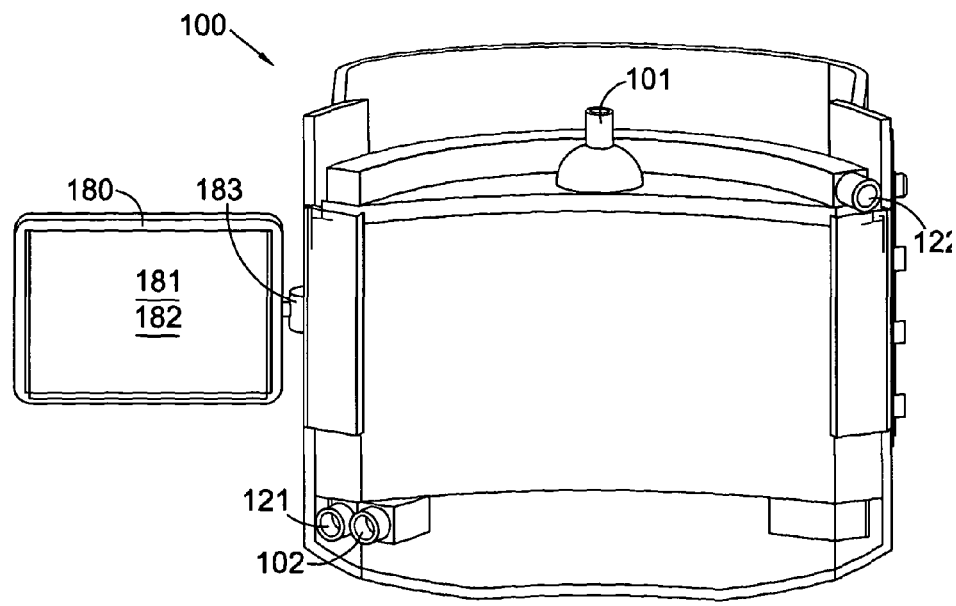
FIG. 2(b) an elevated rear view of the device of FIG. 2(a)
Figure 3A:
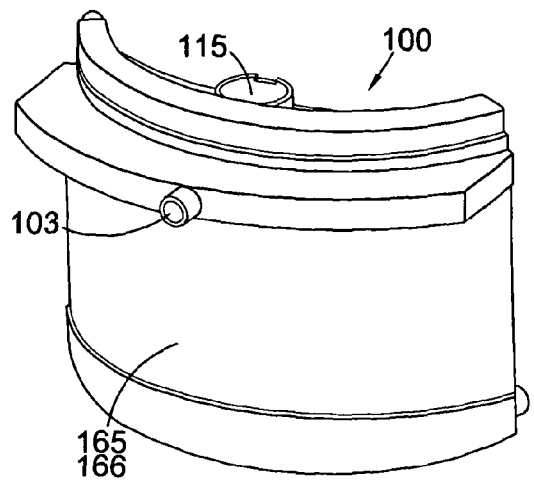
FIG. 3(a) an elevated perspective view of a front portion of the device of FIG. 2(a)
Figure 3B:
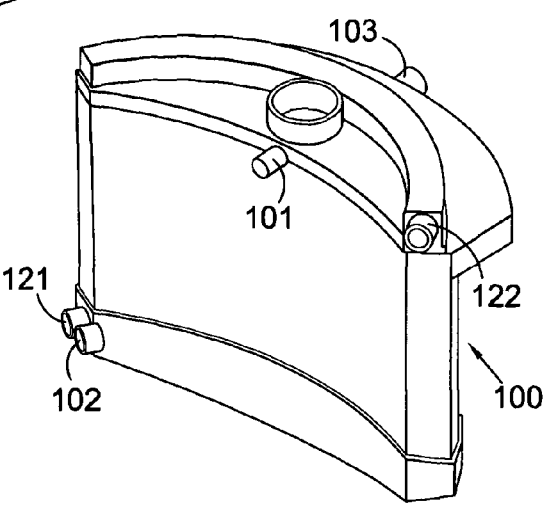
FIG. 3(b) an elevated perspective view of a rear portion of the device of FIG. 2(a)
Figure 3C:
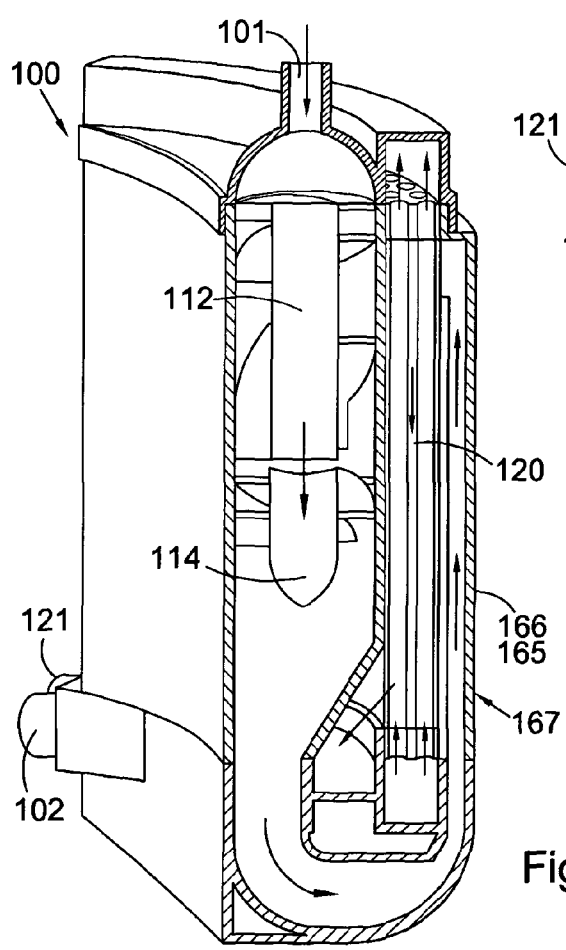
FIG. 3(c) a cross-sectional view of the device of FIG. 2(a)
Figure 4A:
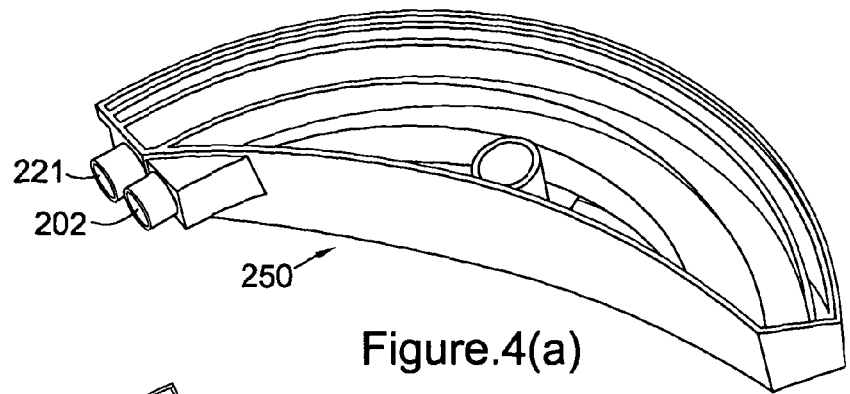
FIG. 4(a) an elevated perspective view of a base portion of a casing of the device of FIG. 3(a)
Figure 4B:
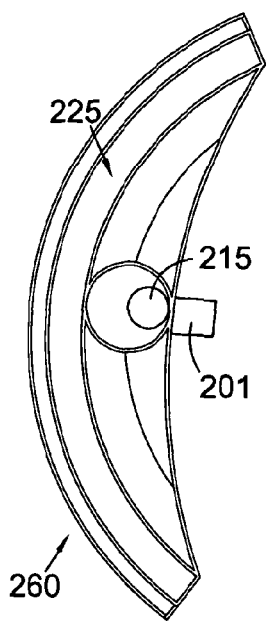
FIG. 4(b) a top view of a central portion of a casing of the device of FIG. 3(a)
Figure 4C:
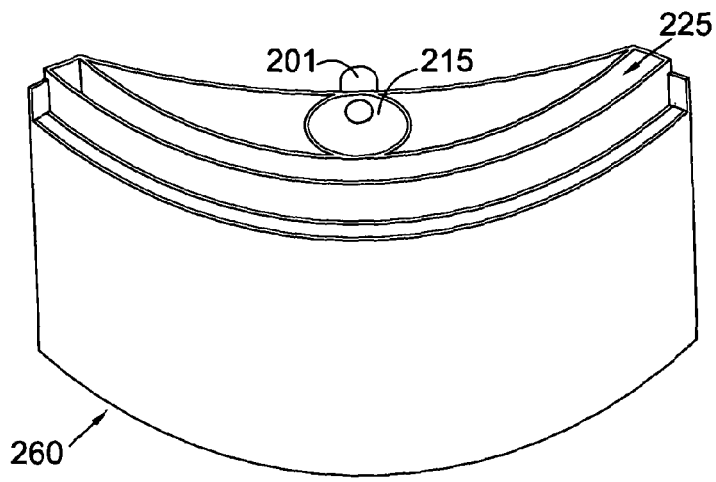
FIG. 4(c) an elevated perspective view of a central portion of a casing of the device of FIG. 3(a)
Figure 4D:
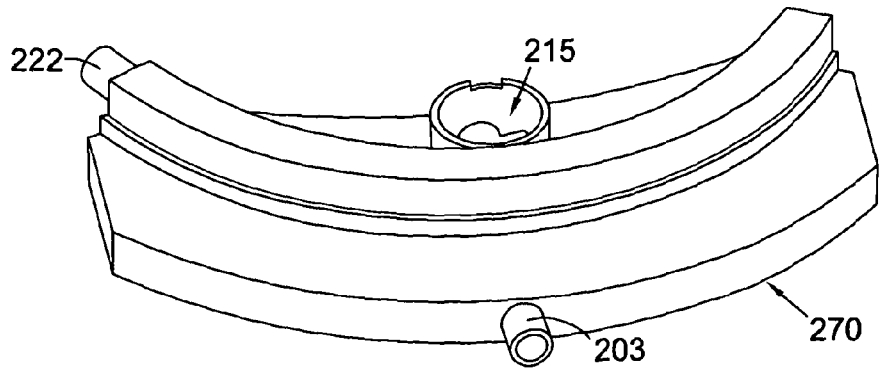
FIG. 4(d) an elevated perspective view of a top portion of a casing of the device of FIG. 3(a)

In FIGS. 2(a), 2(b) and 3(c), the blood inlet 101 is shown in a radial configuration relative to the pump 110 and/or an axis of rotation of the pump impeller 112.

In FIG. 3(b), the blood inlet 101 is shown in an axial configuration relative to the pump 110 and/or an axis of rotation of the pump impeller 112.

The device 100 may comprise either a radial blood inlet 101, or an axial blood inlet 101, or both.

The blood oxygenator 120 is typically a counter-current blood oxygenator and comprises a gas exchange bundle such as a counter-current hollow fibre gas exchange bundle 120.

Typically, when the integrated perfusion device 100 is used in ECMO applications, the blood oxygenator 120 comprises "plasma tight" fibres. When the integrated perfusion device 100 is used in CPB and other applications, the blood oxygenator 120 comprises "non-plasma-tight" fibres.

The blood oxygenator 120 is capable of oxygenating blood processed in the perfusion device 100.

Advantageously, the blood oxygenator 120 may also be capable of removing at least part, e.g. a predetermined amount, of the carbon dioxide present in the blood to be processed. The carbon dioxide may be released from the blood oxygenator 120, e.g. through the ventilating gas outlet 122.

The blood oxygenator 120 is provided near a central portion of the device 100, and is, in use, substantially surrounded by the blood flow path. By such provision the contact surface area between the blood and the oxygenator 120 is maximised, and efficiency of oxygenation is optimised.

The blood oxygenator 120 is provided along a portion of the blood flow path disposed between the blood inlet 101 and the blood outlet 102.

In one embodiment, the integrated perfusion device 100 further comprises a blood gate (not shown) configured to be capable of diverting blood flow within or inside the device 100 so as to bypass the blood oxygenator 120. The blood gate is provided along the blood flow path between the blood inlet 101 and the blood oxygenator 120.

The blood gate has an open configuration and a closed configuration. In an open configuration, the blood gate allows blood flow along the blood flow path between the blood inlet 101 and the blood outlet 102 so as to allow passage through the blood oxygenator 120. In a closed configuration, the blood gate prevents blood flow through the blood oxygenator 120.

As shown in FIGS. 2(a), 3(a) and 3(b), the device comprises a second or bypass blood outlet 103 to allow outflow of blood when the blood gate is in a closed configuration.

When the blood gate is in a closed configuration, the blood flow path is provided between the blood inlet 101 and the second or bypass blood outlet 103.

In this embodiment, the integrated perfusion device 100 further comprises a plurality of heat control units 140 capable of controlling and/or regulating blood temperature.

Conveniently, the heat control units 140 comprise the heat exchange interface 130.

Each heat control units 140 comprises a solid state heating and/or cooling source 141. By such provision the need for a heating/cooling fluid supply, e.g. a water supply, to control blood temperature is eliminated. Further, the solid state heating and/or cooling sources 141 are integrated into the perfusion device 100 thus reducing size of the device 100.

The heating and/or cooling sources 141 are capable of both heating and cooling, and in this embodiment comprise a Peltier device 142. By such provision reliable, rapid temperature control can be achieved. Further, Peltier devices are relatively inexpensive and are therefore suitable for use in the single use perfusion device 100.

The Peltier devices 142 are connected to a power source 145 by Peltier wiring 146. In this embodiment, the power source 145 comprises one or more batteries. By such provision the need for mains power supply to control blood temperate is eliminated.

The Peltier devices 142 are capable of regulating blood temperature in the range of 10-40° C., preferably the range of 18-38° C.

Typically, the heat exchange interface 130 comprises one or more heat exchangers 131 which are in contact with the Peltier devices 142.

Typically, a first side or portion of the heat exchangers 131 is in contact with the blood to be processed.

Advantageously, the first side or portion of the heat exchangers 131 is provided at or near at least a portion the blood flow path between the blood inlet 101 and the blood outlet 102. In this embodiment, the first side or portion of the heat exchangers 131 is provided at or near at least a portion the blood flow path between the blood inlet 101 and the bypass blood outlet 103. By such provision the device is capable of controlling and/or regulating blood temperature even when the blood gate is in a closed configuration.

In this embodiment, a second or opposite side 132 of the heat exchangers 131 is in contact with a thermo-conductive portion, e.g. a thermo-conductive gel 147 which is provided between the second side 132 of the heat exchangers 131 and the Peltier devices 142.

Typically, the heat exchangers 131 are made of a thermo-conductive material. In this embodiment, the heat exchangers 131 are made of aluminium. In an alternative embodiment, the heat exchangers 131 may be made from a synthetic material such as a polymeric material or a metal/polymer composite material.

The Peltier devices 142 are be provided on an external portion 165 of the perfusion device 100, e.g. on an external wall 166 of a front side 167 of the device 100.

The heat exchangers 131 form part of an external portion 165 of the perfusion device 100, e.g. of an external wall 166 of a front side 167 of the device 100.

For clarity purposes, FIG. 2 show only two Peltier devices 142 associated with the device 100. However, the integrated perfusion device 100 typically comprises 4-8 Peltier devices 142.

Figure 2C:
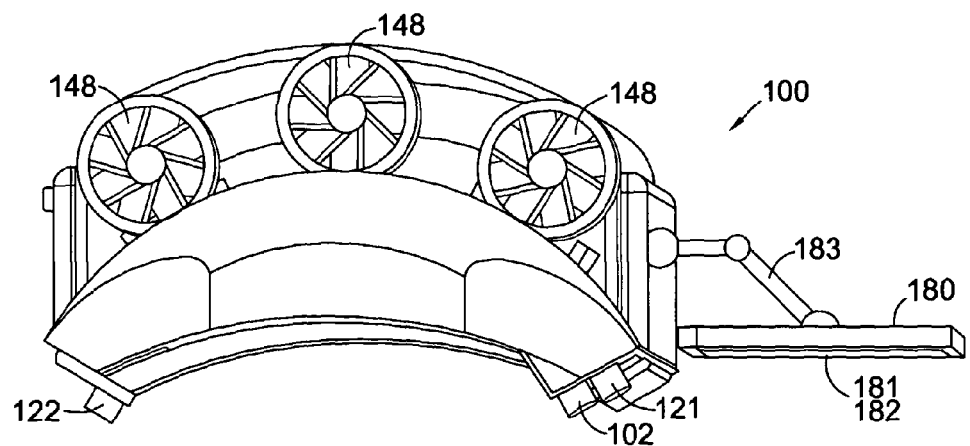
FIG. 2(c) an bottom view of the device of FIG. 2(a)

As shown in FIG. 2(c), the device is preferably equipped with cooling fans 148 for cooling the Peltier devices.

Advantageously, as shown on FIGS. 2(b) and 2(c), the integrated perfusion device 100 further comprises a control unit 180 which controls or interacts with the blood pump 110 so as to be capable of regulating the inlet and/or the outlet blood flow.

The control unit 180 typically comprises a user interface 181 which may display, e.g. outlet blood flow rate, inlet blood flow rate, venous and/or arterial oxygen levels, and/or air bubble levels.

In this embodiment, the user interface 181 comprises an LCD touchpad screen 182.

The control unit 180 is connected to the perfusion device 100 by an optionally adjustable arm 183.

Conveniently, the control unit 180 is in communication with one or more outlet blood flow sensors, one or more inlet blood flow sensors, one or more oxygen sensors and/or one or more bubble detectors (not shown).

The control unit 180 comprises an automated mode in which the control unit 180 automatically or semi-automatically controls and/or adjusts the blood pump flow rate when the inlet and/or outlet blood flow is outside a predetermined range.

In the automated mode, the control unit 180 automatically controls and/or adjusts the ventilating gas inlet flow rate, and/or the oxygen ratio of a ventilating gas supply or blender connected to the ventilating gas inlet 121, when the venous and/or arterial oxygen levels are outside a predetermined range.

By providing an automated mode, the device 100 may be suitable for use in non-specialist ECMO or CPB centres, and/or by non-specialist personnel.

The control unit 180 also comprises a manual mode in which a user may manually control and/or adjust the blood pump flow rate, e.g. though the user interface 181, when the inlet and/or outlet blood flow is outside a range of predetermined flow rates.

In the manual mode, the control unit 180 allows a user to manually control and/or adjust, e.g. though the user interface 181, the ventilating gas inlet flow rate, and/or the oxygen ratio of a gas ventilating gas blender connected to the ventilating gas inlet 121, when the venous and/or arterial oxygen levels are outside a predetermined range. The control unit 180 also allows a user to operate the blood flow gate (not shown).

Conveniently, the control unit 180 further comprises an alarm and/or warning display (not shown), e.g. visual or sound display, which is in communication with, e.g. the oxygen sensor(s), the bubble detector(s), and or the outlet and/or inlet blood flow sensor(s).

The oxygen sensor(s) may trigger activation of the alarm and/or warning display when the oxygen sensor(s) detects that venous and/or arterial oxygen levels are outside a predetermined range.

The bubble detector(s) may trigger activation of the alarm and/or warning display when the bubble detector(s) detects that air bubble levels in the blood flow are above a predetermined level.

The outlet and/or inlet blood flow sensor(s) may trigger activation of the alarm and/or warning display when the outlet and/or inlet blood flow sensor(s) detects that outlet and/or inlet blood flow rate are outside a predetermined range.

Conveniently, the control unit 180 can be accessed, controlled and/or operated by Bluetooth™ technology. By such provision a user may be able to operate the control unit 180 remotely, e.g. using a Bluetooth™-enabled mobile phone.

Referring now to FIGS. 4(*a*) to 4(*d*), there is shown a casing, generally designated 200, for use in the device 100 of FIGS. 2(*a*) to 3(*c*), same part being denoted by like numerals, but supplemented by '100'.

The casing 200 defines a blood flow path and comprises a blood inlet 201, a blood outlet 202, a ventilating gas inlet 221, and a ventilating gas outlet 222.

Preferably, the casing 200 is a single use or disposable casing.

The casing 200 comprises a pump receiving portion 215 configured to receive a blood pump 210, e.g. a vortex blood pump 211.

The casing 200 comprises an oxygenator receiving portion 225 configured to receive a blood oxygenator 220.

In an alternative embodiment, the blood oxygenator 220 may form, part of the casing 200 itself, e.g. be formed integrally with the casing 200.

The blood oxygenator 220 is provided near a central part of the casing, and is, in use, substantially surrounded by the blood flow path.

The casing 200 may further comprise a blood gate receiving portion (not shown) arranged to receive a blood gate (not shown) configured to be capable of diverting blood flow within or inside the device so as to bypass the blood oxygenator 220.

Alternatively, the blood gate may form part of the casing 200 itself, e.g. be formed integrally with the casing 200.

The casing 200 comprises a second or bypass blood outlet 203 to allow blood outflow when the at least one blood gate is in a closed configuration.

In this embodiment, the casing 200 comprises a base portion 250, a top portion 270, and a central portion 260 provided between the base portion 250 and the top portion 260. The base portion 250, top portion 270, and central portion 260 are connectable, e.g. sealably connectable, to each other so as to be airtight and watertight.

In an alternative embodiment, the casing 200 may comprise an integral casing unit.

Typically, the blood inlet 201 is connected to a venous blood vessel of e.g. a patient, limb or organ, by a blood inlet conduit or tube (not shown).

Typically, the blood outlet 202 and/or the bypass blood outlet 203 is connected to an arterial blood vessel of e.g. a patient, limb or organ, by a blood inlet conduit or tube (not shown).

The ventilating gas inlet 221 is connected to a source of ventilating gas for supply to the blood oxygenator 220, by e.g. a gas inlet conduit or tube (not shown).

The ventilating gas outlet 222 is connected to a source of ventilating gas, a gas treatment unit, or a gas disposal unit for release of exhausted gas from the blood oxygenator 220, by e.g. a gas outlet conduit or tube (not shown).

The width and/or height of the casing 200 is typically in the range of approximately 5-50 cm, and more typically in the range of approximately 10-30 cm.

The casing 200 is equipped with a control unit (not shown) which is connected to the casing 200 by an optionally adjustable arm.

In an alternative embodiment, the control unit may be provided within a control unit receiving portion.

In this embodiment, the casing 200 is connected to one or more heat control units (not shown) capable of controlling and/or regulating the temperature of blood circulating through the blood flow path. Configuration of the heat control units is fully described in relation to FIGS. 2(*a*) to 3(*c*) and is not repeated here for brevity.

Alternatively, the casing 200 may comprise at least one receiving portion (not shown) for receiving the heat control unit(s).

In an alternative embodiment, the casing 200 may not be connected to a heat control unit and/or may not comprise a heat control unit receiving portion. In such instance temperature control may be performed by controlling the temperature of the ventilating gas supplied to the oxygenator 120.

Figure 5A:
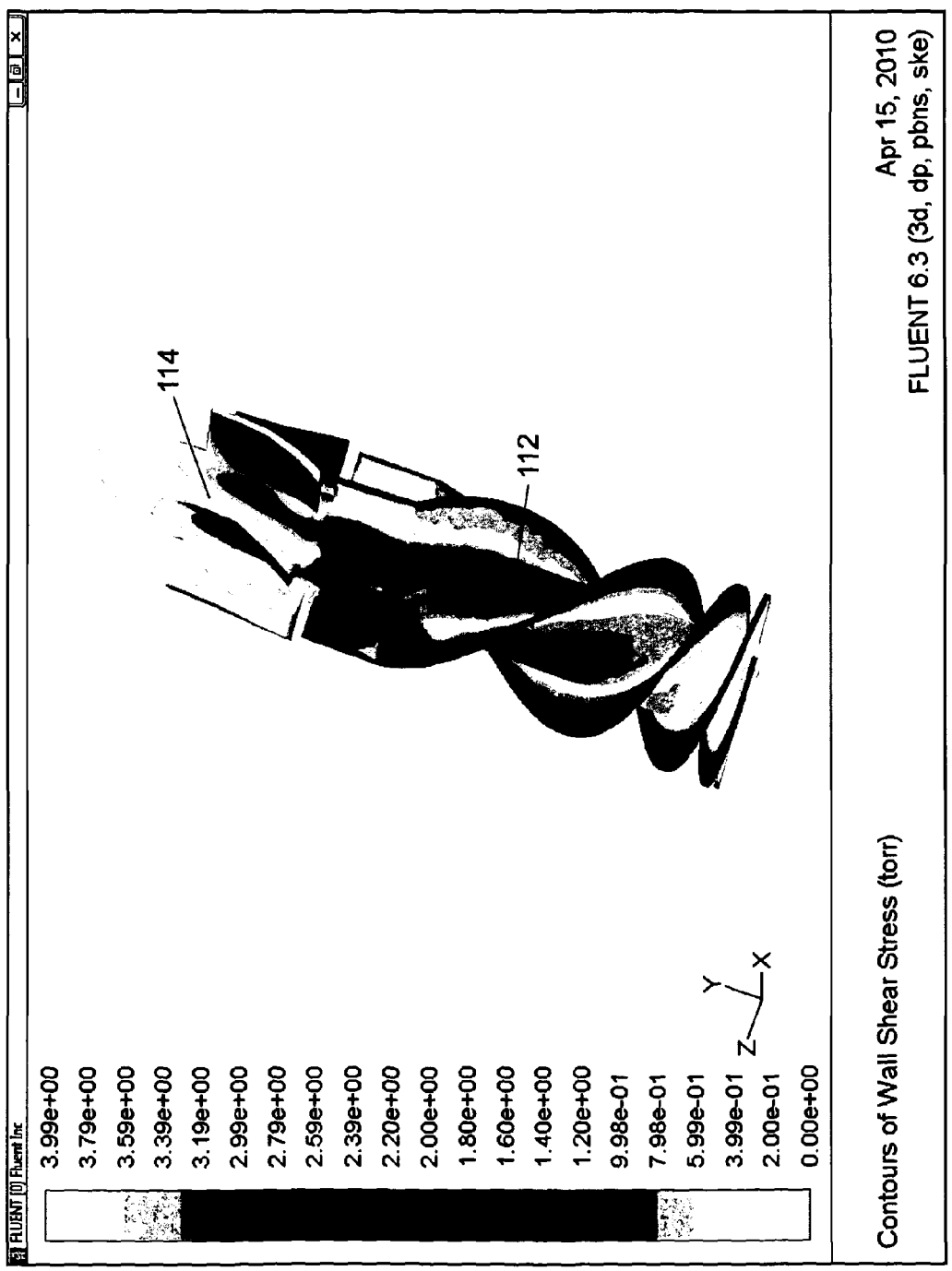
FIG. 5(a) a computer-imaging view of an impeller of a pump of the device of FIG. 2(a)
Figure 5B:
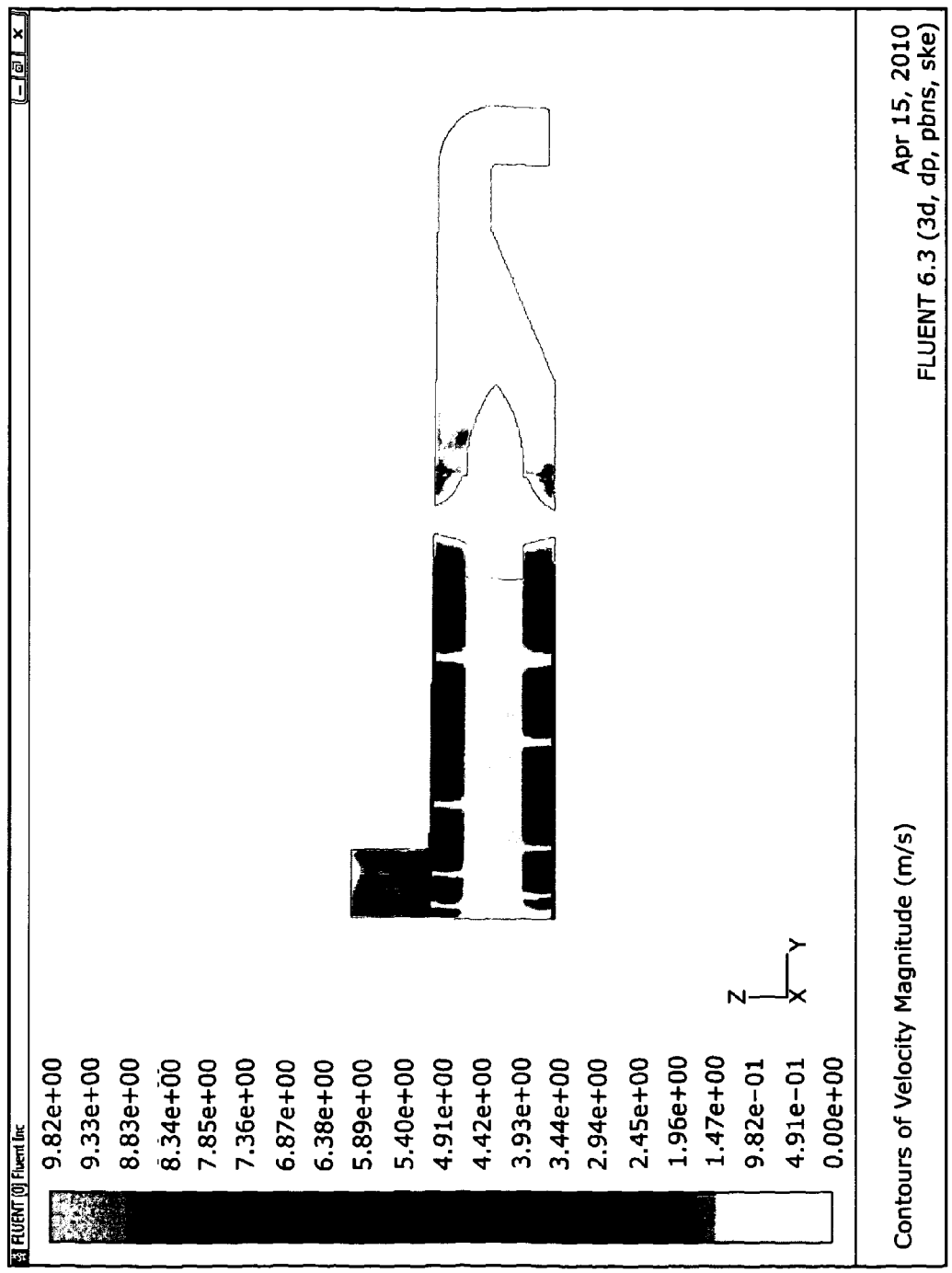
FIG. 5(b) a computer-imaging view of the velocity profile of the impeller of FIG. 5(b)

Referring now to FIGS. 5(*a*) and 5(*b*), there is shown the pump impeller 112 of a pump 110 for use in the device 100 of FIGS. 2(*a*) to 3(*c*) or the casing 200 of FIGS. 4(*a*) to 4(*d*).

The pump 110 is a vortex pump 111. By such provision, the device 100 has very low priming volume and offers a wide range of flow rates.

FIG. 5(*a*) shows a computer-imaging view of the impeller 112 and diffuser 114.

FIG. 5(*b*) shows a computer-imaging view of the velocity profile of the impeller 112, and illustrates how the profile of the impeller 112 has been optimised to suit the requirements of the vortex pump 110 for use in the perfusion device 100.

Figure 6:
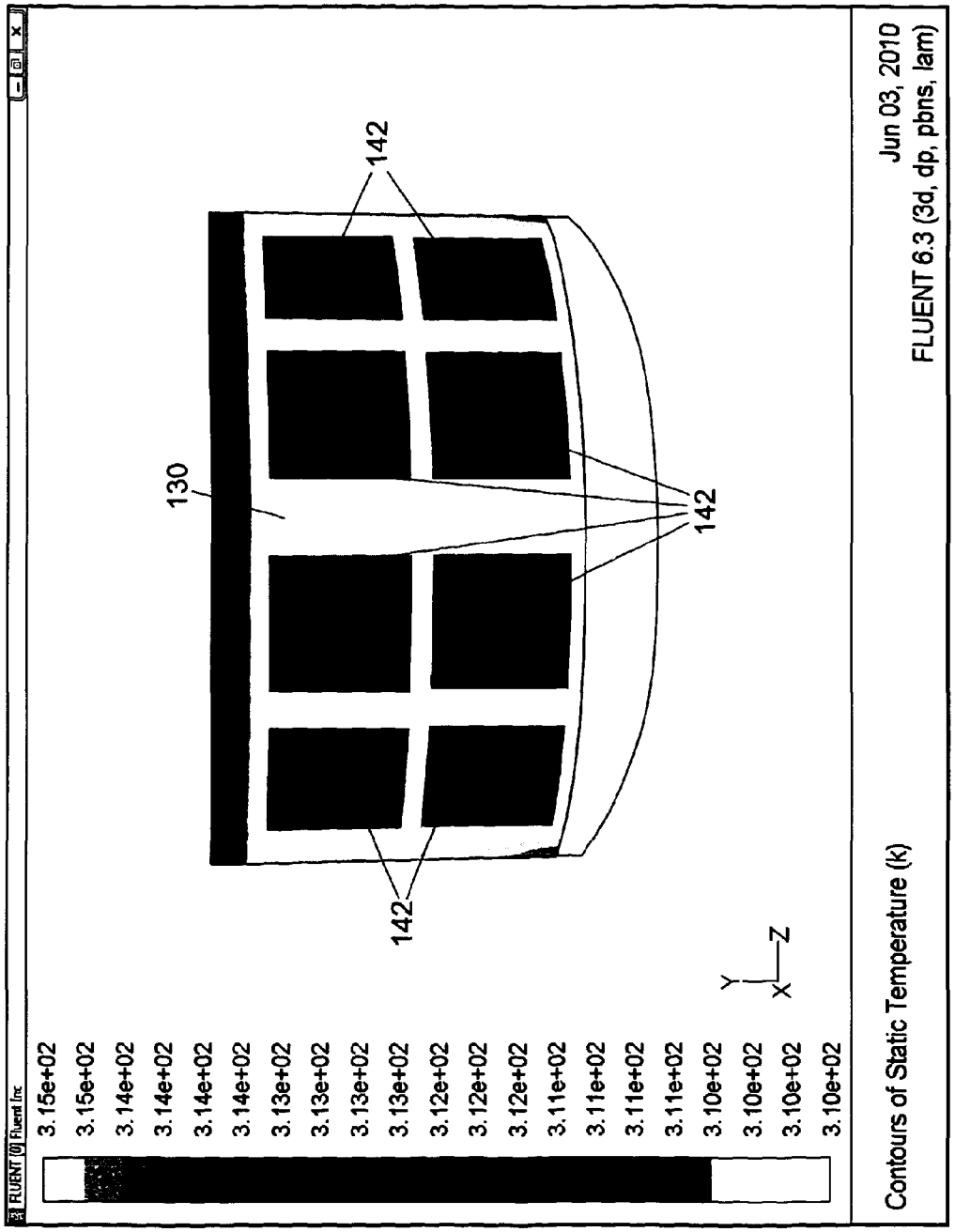
FIG. 6 a computer-modelled static thermal analysis of a heat exchange interface of the device of FIG. 2(a) equipped with 8 Peltier panels.

FIG. 6 shows a computer-modelled static thermal analysis of a heat exchange interface 130 of the device 100 of FIGS. 2(*a*) to 3(*c*) equipped with 8 Peltier panels 142, operating in heating mode.

As can be seen, the heat generated by the Peltier panels 142 is distributed evenly and homogeneously over the heat exchange interface 130.

Similar experiments were conducted with Peltier panels 142 operating in cooling mode, which also revealed even and homogeneous temperature distribution over the heat exchange interface 130.

Figure 7:
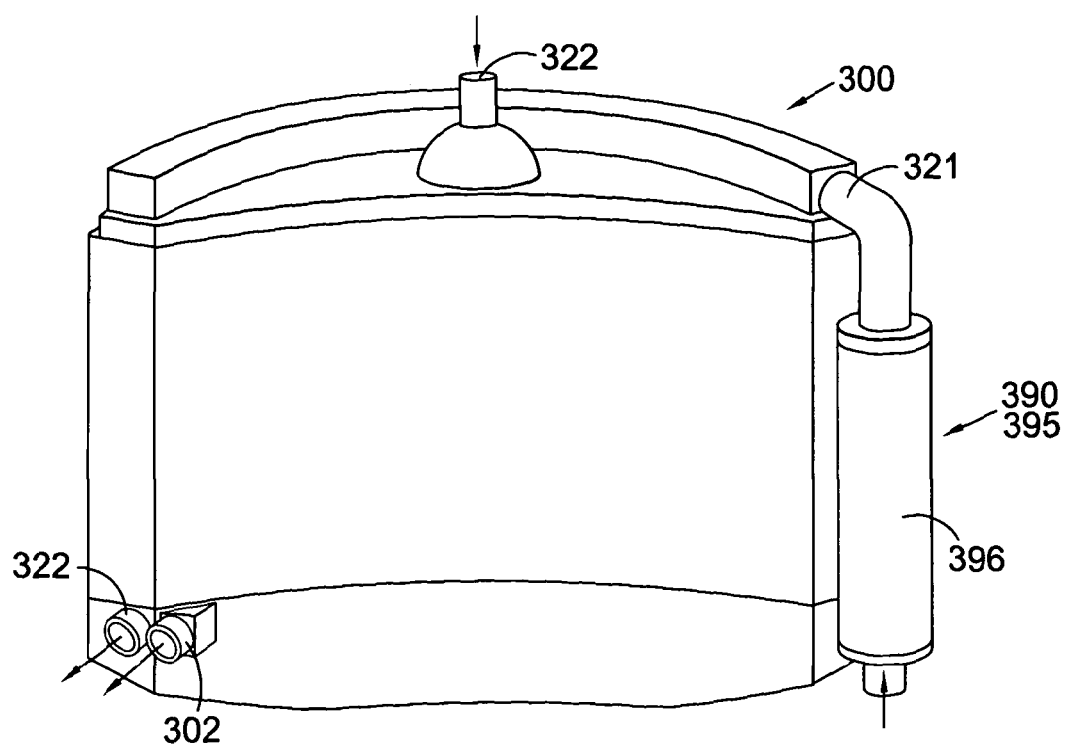
FIG. 7 an elevated rear view of an integrated perfusion device according to a second embodiment of a first aspect of the present invention.

FIG. 7 shows an integrated perfusion device 300 according to a second embodiment of a first aspect of the invention.

The perfusion device 300 is generally similar to the perfusion device 100, like parts being denoted by like numerals, but is devoid of a heat control unit. Thus, temperature control of blood through the perfusion assembly 400 is performed by controlling the temperature of the ventilating gas supplied to the oxygenator 320 of the perfusion device 300.

In this embodiment, temperature control of the ventilating gas is carried out through a solid state gas heat exchanger 390 which comprises a gas expansion chamber 395 which is heated by a heat wrap device 396.

Typically, the gas heat exchanger 390 is provided near or upstream from the gas inlet 321.

In this embodiment, for the purpose of illustration, the gas inlet 321 is provided near a top portion of the perfusion device 300, and the gas outlet 322 is provided near a bottom portion of the perfusion device 300 near the blood outlet 302. In such instance the blood oxygenator 320 is in a concurrent configuration (that is blood flow and gas flow move in the same direction). However, it is understood that, in order to optimise efficiency and performance of the oxygenator 320, the gas inlet 321 and gas outlet 322 mat be provided in an opposite arrangement (similarly to the device 100 of FIGS. 2(a) to 3(d)) so as to provide the oxygenator 320 is in a counter-current configuration.

Figure 8:
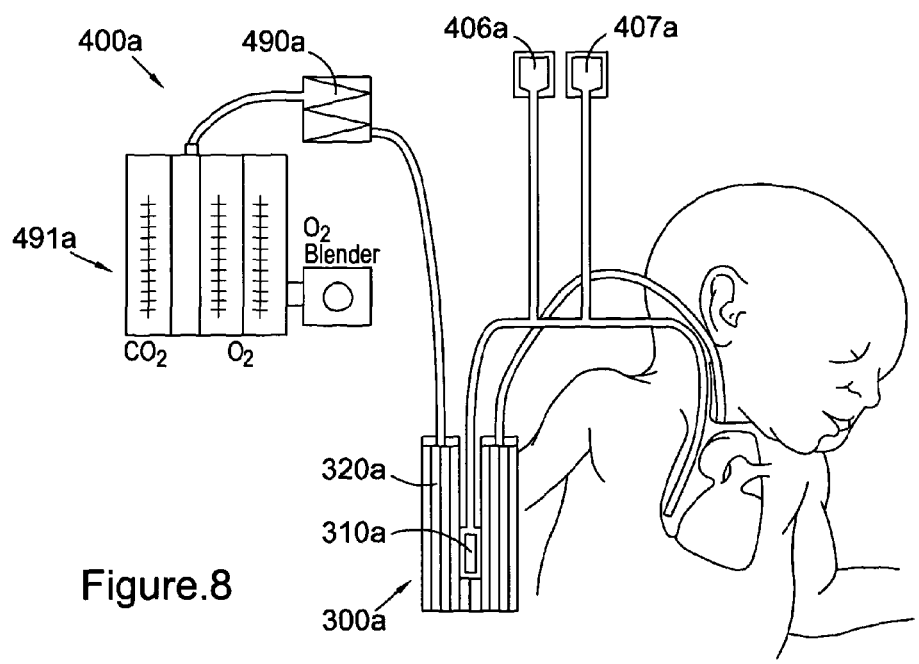
FIG. 8 a schematic representation of a second embodiment of a perfusion assembly according to a fourth aspect of the present invention, comprising the integrated perfusion device of FIG. 7.

FIG. 8 shows an embodiment of a perfusion assembly 400a according to a fourth aspect of the present invention. The perfusion assembly 400a comprises an integrated perfusion device 300a similar to the device 300 of FIG. 7, the gas heat exchanger 490a being provided upstream from the oxygenator 320a.

In this embodiment, temperature control of the ventilating gas is carried out through a gas heat exchanger 490a which comprises a gas expansion chamber which may be heated by a heat wrap device.

The gas heat exchanger 490a is located between the ventilating gas supply 491a and the oxygenator 320a of the perfusion device 300a.

The perfusion assembly 400a further comprises a reservoir of fluids 406a and heparin 407a for treating a patient's blood.

Figure 9:
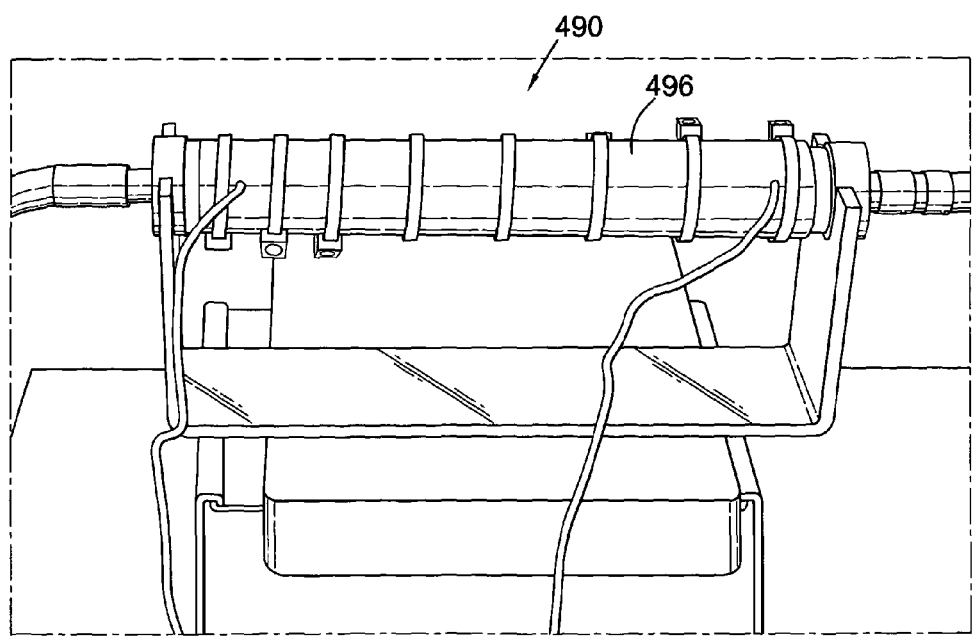
FIG. 9 an elevated side view of a solid state heat exchanger of the perfusion device of FIG. 7 or the perfusion assembly of FIG. 8.

FIG. 9 shows a solid state gas heat exchanger 490, as used in the perfusion assembly 400a of FIG. 8. The state gas heat exchanger 490 comprises a gas expansion chamber (not shown) which is heated by a heat wrap device 496.

Figure 10:
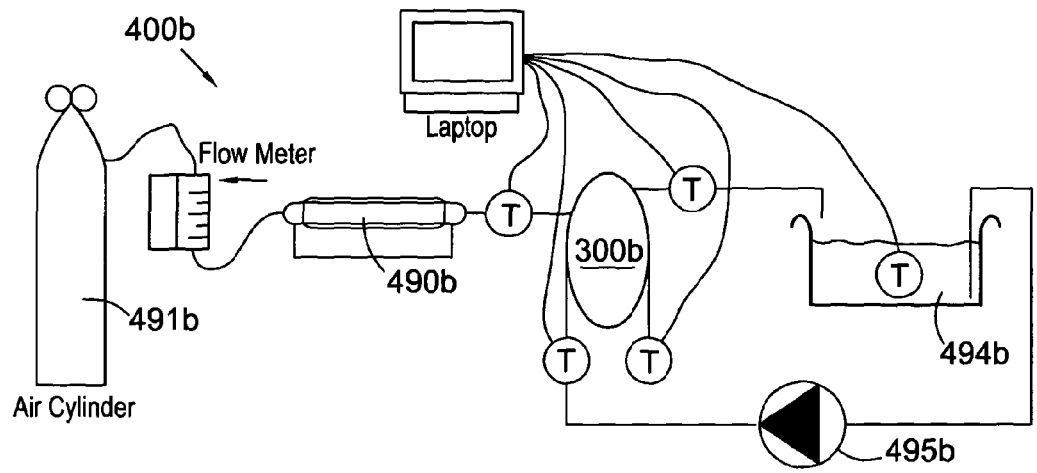
FIG. 10 an alternative embodiment to the assembly of FIG. 8, comprising the integrated perfusion device of FIG. 7.

FIG. 10 shows an embodiment of a perfusion assembly 400b. The perfusion assembly 400b is similar to the perfusion assembly 400a of FIG. 8. However, in perfusion assembly 400b, the fluid circulated through the oxygenator 320b of the perfusion device 300b was water. Water was chosen as a convenient and cost-effective way of assessing the performance of the solid state gas heat exchanger 490b of the assembly 400b. The stand alone DC supply powering the gas heat exchanger 490b was set to 25 volts. The air was allowed to exit from the oxygenator 320b to the atmosphere.

Figure 11A:
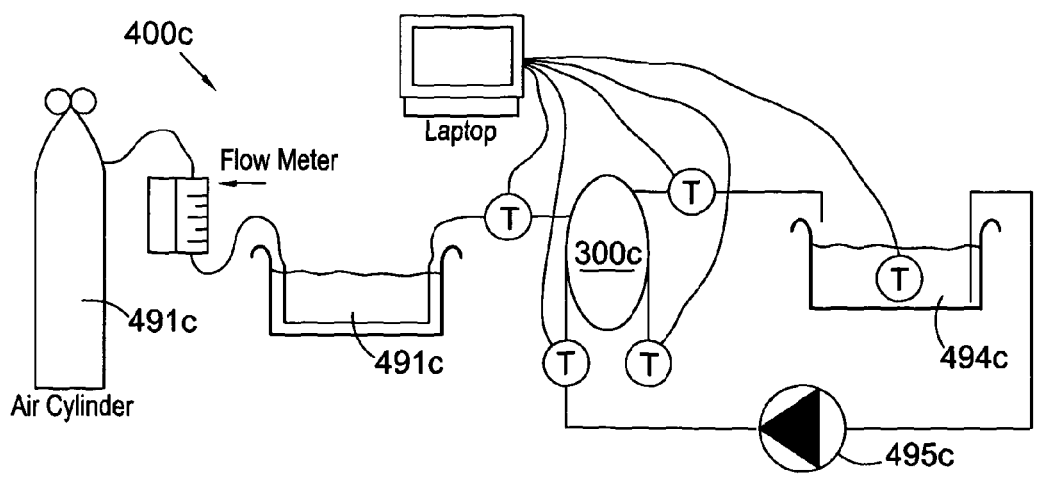
FIG. 11a an alternative embodiment to the assembly of FIG. 8, comprising the integrated perfusion device of FIG. 7, the temperature of the ventilating gas being heated controlled by a water bath.
Figure 11B:
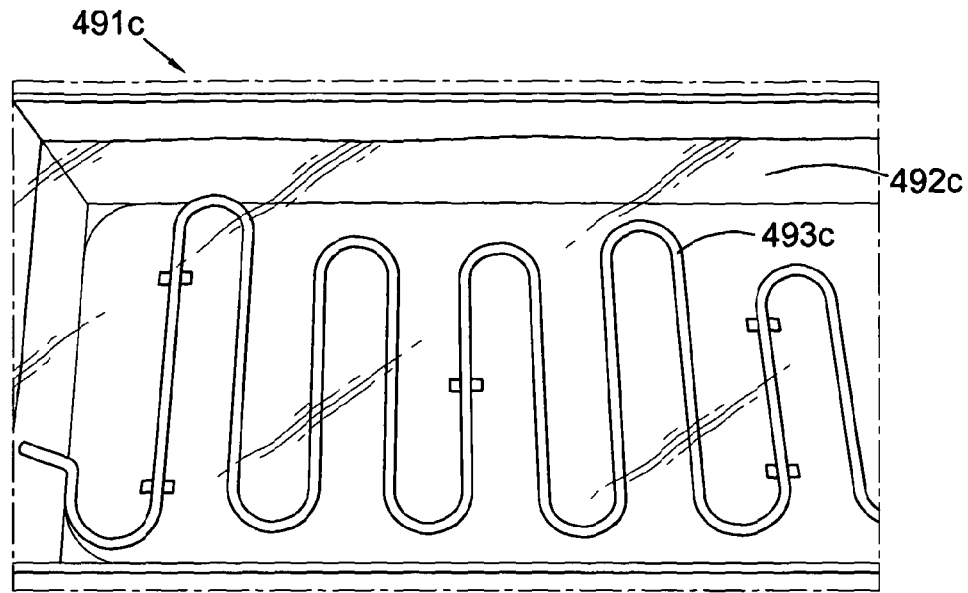

FIG. 11a shows an alternative embodiment of a perfusion assembly 400c. The perfusion assembly 400c is similar to the perfusion assembly 400b of FIG. 10. However, in perfusion assembly 400c, the gas heat exchanger comprises a water bath 491c. The water bath 491c is shown in more detail in FIG. 11b, and comprises a heated water tank 492c, and copper tubing 493c immersed in the heated water tank 492c. Flow of ventilating gas through copper tubing 493c allows heating of the ventilating gas prior to delivery to the oxygenator 420c of perfusion device 300c. In this embodiment the water bath 491c was set at 60° C.

In both assemblies 400b, 400c, a water bath 494b, 494c was set to 36° C., to simulate the patient's blood. Water was pumped from the water bath 494b, 494c via a roller pump 495b, 495c, set at 500 mL/min, through the membrane oxygenator 320b, 320c of the integrated perfusion device 300b, 300c, before being returned to the water bath 494b, 494c.

A number of temperature probes T measured water temperature in the water bath 494b, 494c, water temperature at the inlet and outlet of the oxygenator 320b, 320c of the integrated perfusion device 300b, 300c, and air temperature at the inlet and outlet of the oxygenator 320b, 320c of the integrated perfusion device 300b, 300c. A Physitemp MT29/3 needle probe was used to measure the air inlet temperature while all other temperature measurements were made using Hype thermocouples.

Figure 21A:
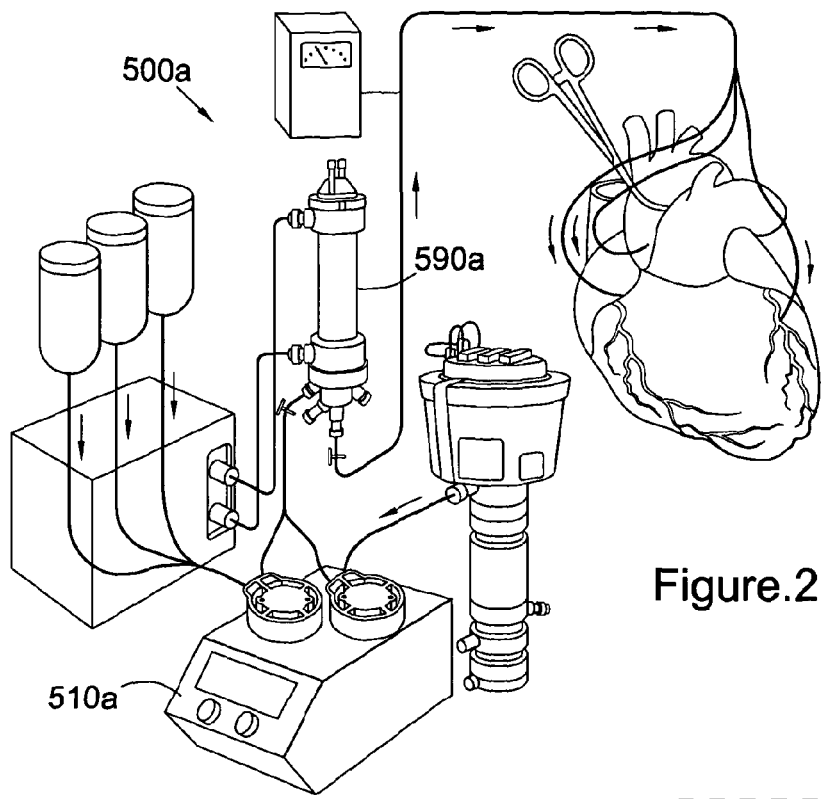
FIG. 21(a) a first embodiment of a conventional cardioplegic assembly according to the prior art.

FIG. 21(a) shows a first embodiment of a conventional cardioplegic assembly 500a according to the prior art. A double roller pump 510a is used to deliver blood and a cardioplegic solution to a conventional heat exchanger 590a through a single delivery tube. A large heater-cooler unit is used to supply temperature-controlled water to the heat exchanger 590a.

Figure 21B:
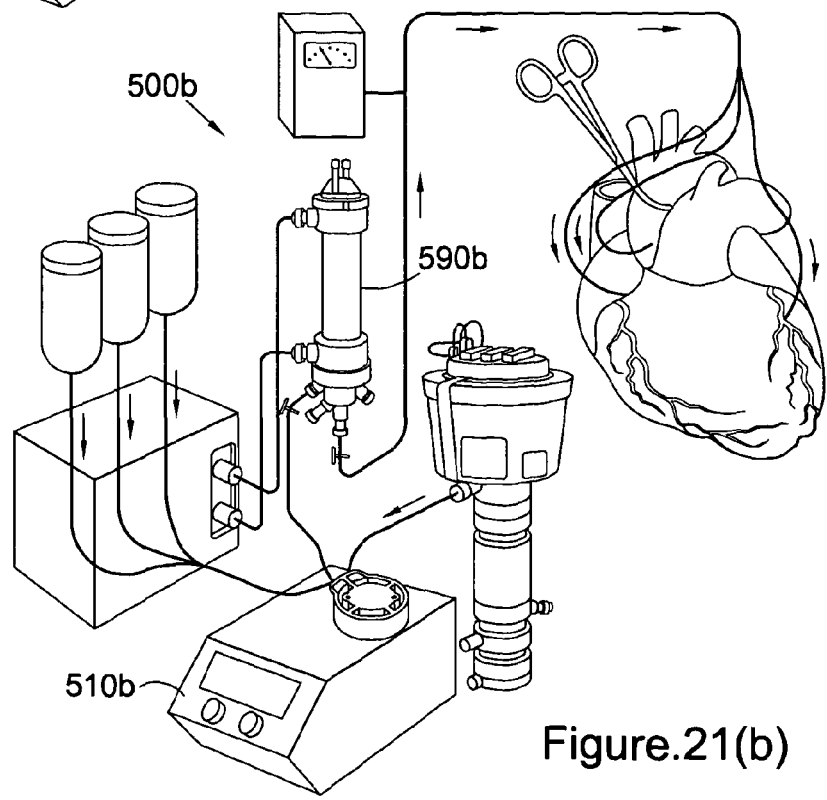
FIG. 21(b) a second embodiment of a conventional cardioplegic assembly according to the prior art.

FIG. 21(b) shows a second embodiment of a conventional cardioplegic assembly 500b according to the prior art. The assembly 500b is generally similar to the assembly 500 of FIG. 21(a), like parts being denoted by like numerals. However, in the embodiment of FIG. 21(b), the pump is a single roller pump 510b with a double lumen delivery tube designed to provide the appropriate mixture of blood and cardioplegia solution to the heat exchanger 590b.

Figure 22:
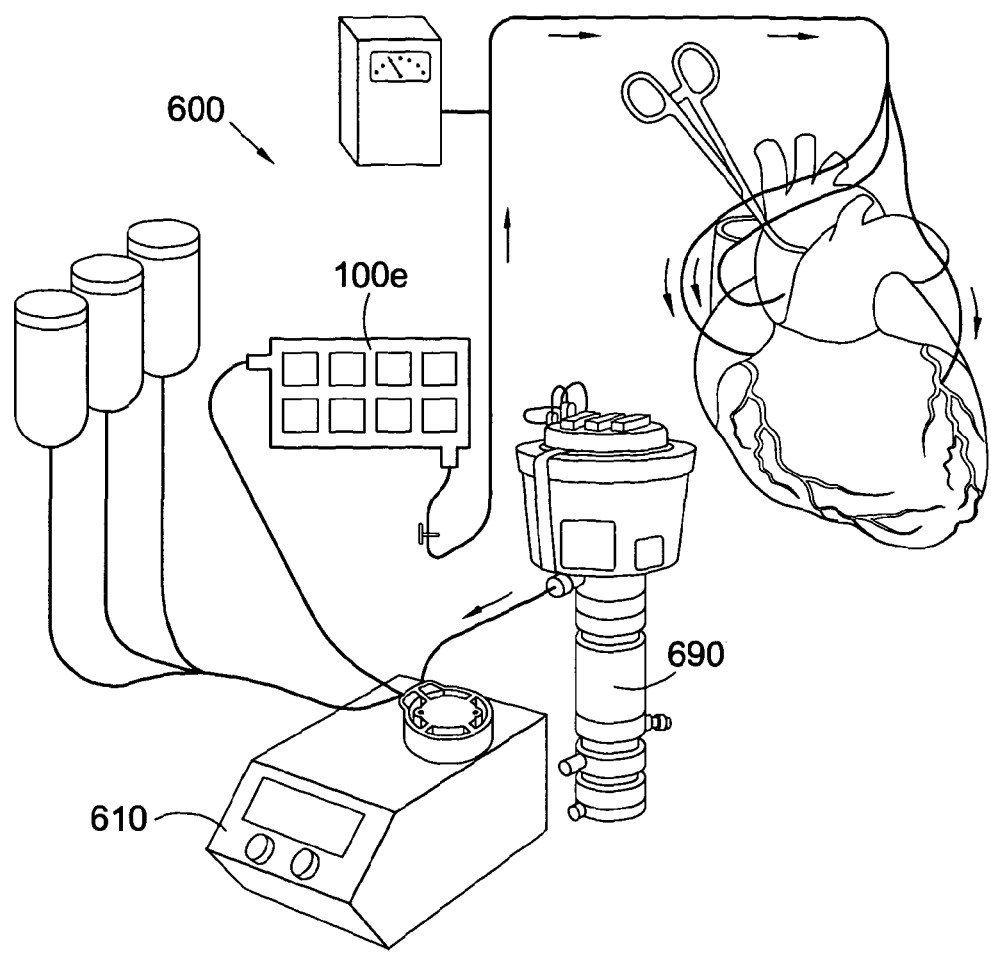
FIG. 22 a schematic view of a cardioplegic assembly according to an embodiment of a seventh aspect of the present invention.

FIG. 22 shows a schematic view of a cardioplegic assembly 600 according to an embodiment of a seventh aspect of the present invention. As in the assembly 500b of FIG. 21(b), the cardioplegic assembly 600 uses a single roller pump 610. However, the assembly 600 comprises a heat control unit 100e. In this embodiment, the heat control unit comprises the heat control unit 100e of FIG. 16(a). However, in alternative embodiments, the heat control unit may comprise the heat control unit 100b of FIG. 13(a) or the heat control unit 100c of FIG. 14.

Experiments and Results

Figure 12A:
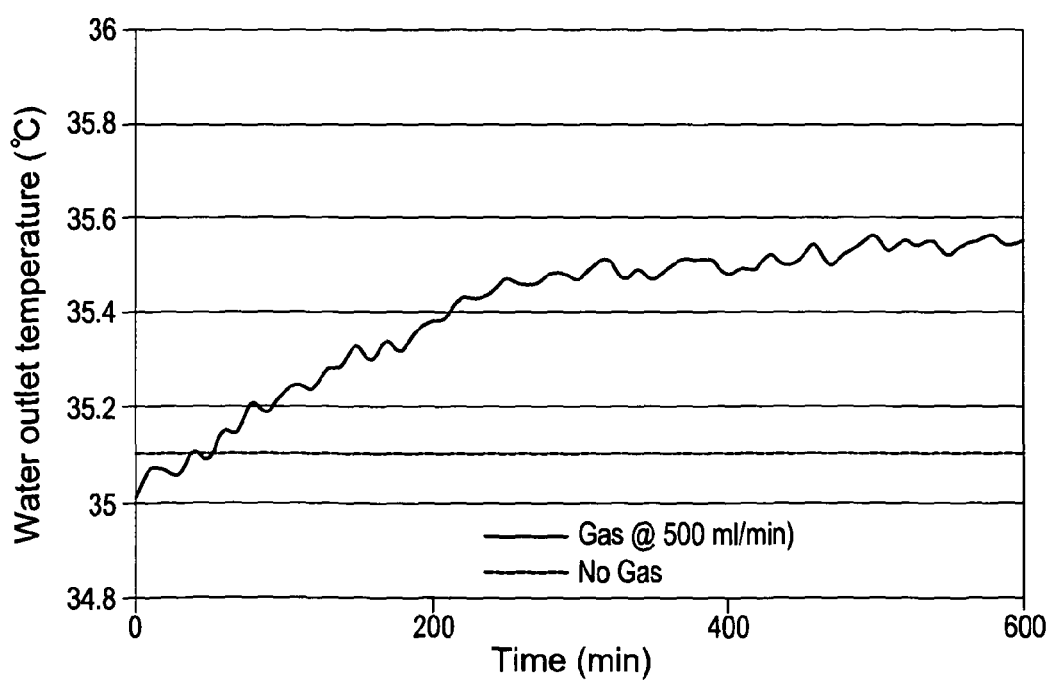
FIG. 12a a graph showing the temperature of a fluid processed using the perfusion assembly of FIG. 10 over time.
Figure 12B:
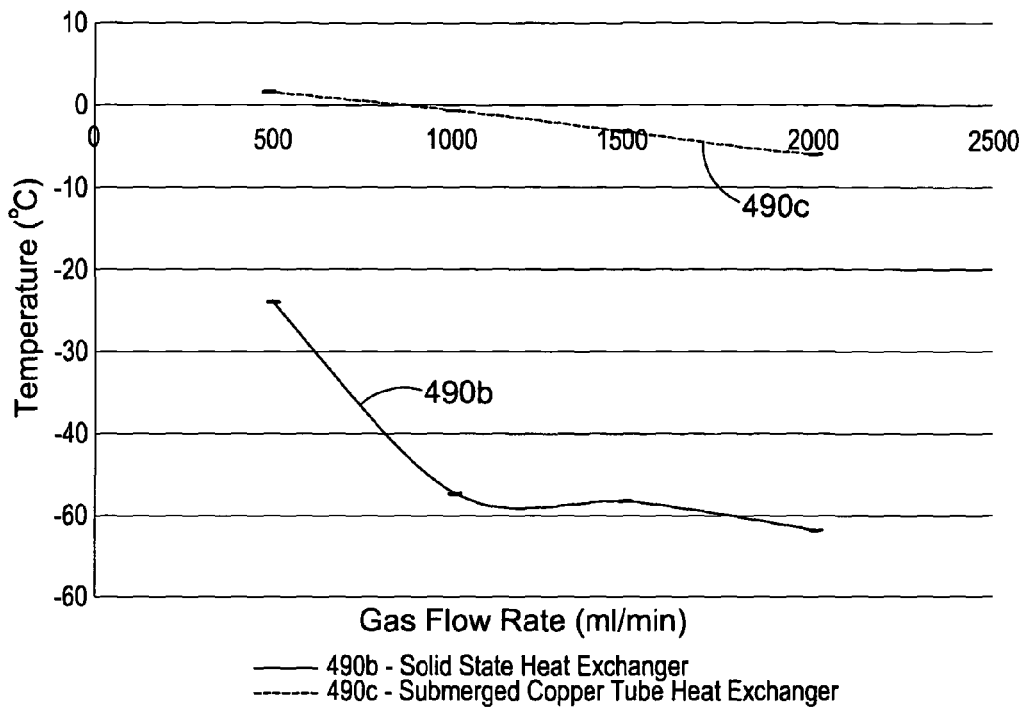
Figure 12C:
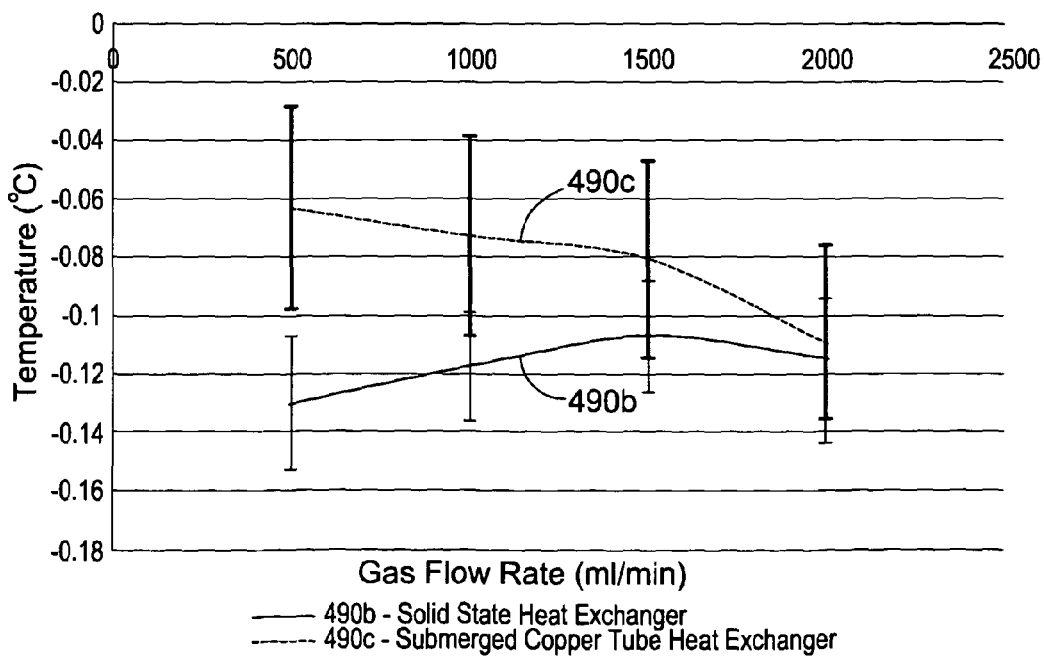

The results of the temperature measurements taken for assemblies 10 and 11a are shown on FIGS. 12a to 12c.

As shown on FIG. 12a, it can be seen that, using the perfusion assembly 400b of FIG. 10, it is possible to increase the outlet temperature of the water being processed through the oxygenator 320b by supplying ventilating gas which has been heated through gas heat exchanger 490b. Therefore, it should be possible to maintain blood temperature at normothermic levels using assembly 400b, at least under neonatal ECMO conditions.

FIG. 12b shows the difference in gas temperature across the oxygenator 320b, 320c of perfusion device 300b, 300c for both heat exchangers 490b and 490c. It can be seen that the solid state heat exchanger 490b is able to provide gas to the system at a significantly higher temperature than was previously achieved with the submerged copper tube exchanger 490c.

FIG. 12c shows the difference in water temperature across the oxygenator 320b, 320c of perfusion device 300b, 300c for both heat exchangers 490b and 490c. It can be seen that in both cases the efficacy of heated gas to act as a positive heat source to the water passing through the oxygenator 320b, 320c is limited.

Experiments were also carried out to assess the heat exchanging performance of the integrated perfusion device 100 as described with reference to FIGS. 2(a) to 3(c). To that end a number of modified devices were designed.

Figure 13A:
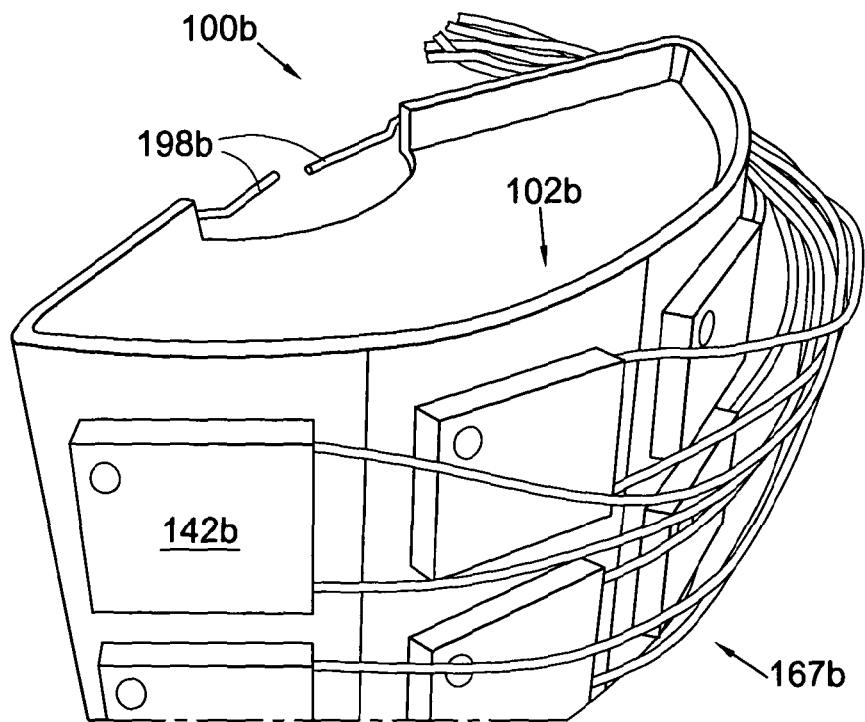
FIG. 13a an elevated perspective view of an embodiment of an integrated perfusion device according the invention.
Figure 13B:
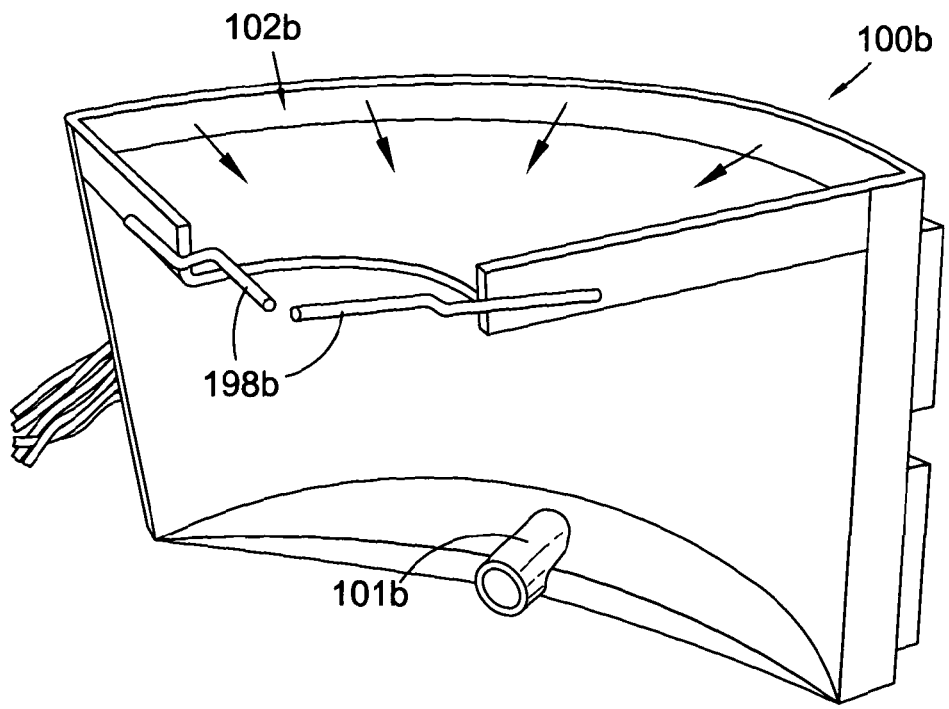
FIG. 13b an elevated rear view of the device of FIG. 13(a)
Figure 13C:
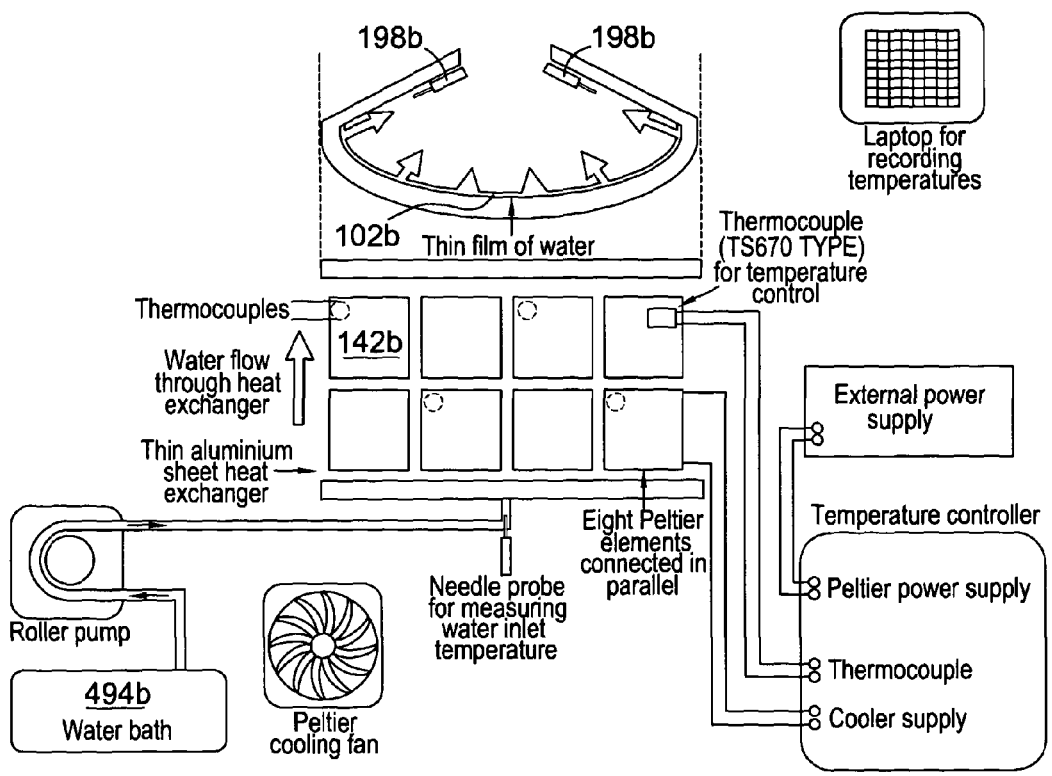
FIG. 13c a schematic view of the device of FIG. 13(a)

The following aspects of device design/configuration were investigated in the experiments detailed below:
 curved/flat device shape,
 different materials (polymer/aluminium)
 thickness of blood film (3 mm/5 mm)
 presence of fins to disrupt fluid
 Peltier element array connected in series/parallel
 Temperature controlled using temperature controller/controlled manually
 Peltier elements controlled individually (manual multiplexing)
 fluid being heated (water/blood)
 flow rate of fluid (blood/water)
 temperature of Peltier elements FIGS. 13a and 13b show respectively an elevated perspective view and an elevated rear view of a modified integrated perfusion device 100b. FIG. 13c shows a schematic view of the device 100b. The modified integrated perfusion device 100b of FIGS. 13a and 13b is a simplified version of the device 100 of FIGS. 2(a) to 3(c), like part being denoted by like numerals, supplemented by the suffix "b".

In this embodiment, the device 100b comprises an open fluid circuit. The fluid inlet 101b is provided near a lower portion of the device 100b. The fluid outlet 102b is provided near a front side 167b and substantially across the width of an upper portion of the device 100b, and flows upon a top portion of the device 100b where fluid outlet temperature measurements were made using probes 198b.

The device 100b was mainly made of rapid prototyped polymer. The device 100b was also comprised thin aluminium sheet portions on a front side 167b thereof for contacting solid state heat exchange Peltier devices 142b.

Water at a set temperature is passed through the device 100b. In these open circuit experiments, water inlet temperature and water outlet temperature were measured in order to determine performance of the device 100b.

The effect of changing the set temperature of the Peltier devices 142b was investigated. Temperatures in these experiments were measured using RS k-type thermocouples, Physitemp MT29/1 needle probes and a TS-67 thermistor, and were recorded using a PicoLog TC-08 USB data logger. The temperatures of the Peltier elements 142b were controlled either by a TETech TC-36-25 RS232 temperature controller based one a 1/32" cycle time, or were manually controlled, using multiple temperature probes and/or multiple power supplies.

Figure 14:
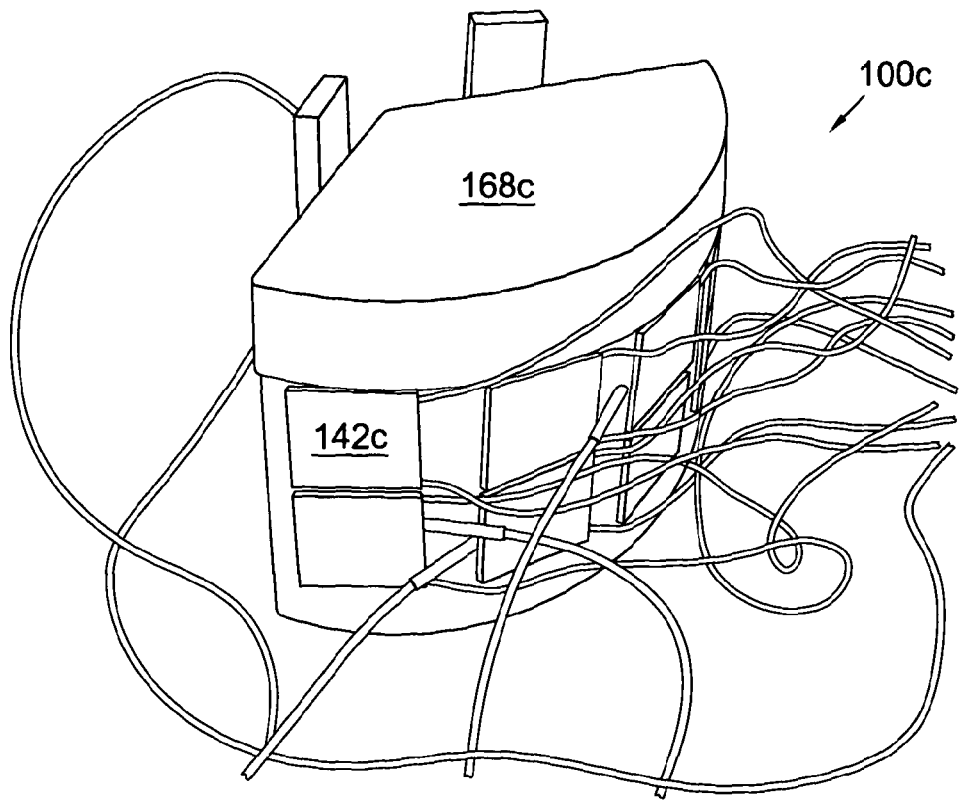
FIG. 14 an elevated perspective view of an embodiment of an integrated perfusion device according the invention.

FIG. 14 shows an elevated perspective view of a modified integrated perfusion device 100c. The modified integrated perfusion device 100c of FIG. 14 is generally similar to the device 100b of FIGS. 13(a) and 13(b), like part being denoted by like numerals, supplemented by the suffix "c". However, the device 100c comprises a top portion 168c defining an enclosed fluid outlet 102c (not shown), where fluid outlet temperature measurements were made using a probe (not shown).

Figure 15:
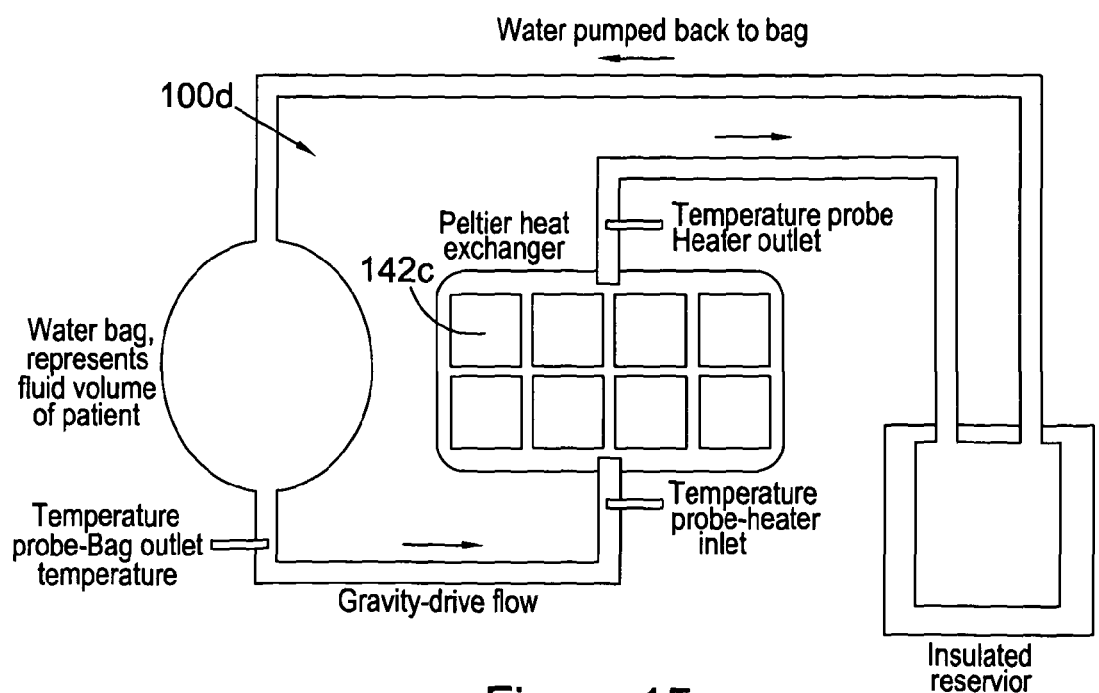
FIG. 15 a schematic view of an embodiment of an integrated perfusion device according the invention.

Experiments were also made using a device 100d comprising a closed loop fluid path rather than an open fluid circuit. FIG. 15 shows a schematic view of the closed loop fluid path device 100d. The modified integrated perfusion device 100d of FIG. 15 is generally similar to the device 100c of FIG. 14, like part being denoted by like numerals, supplemented by the suffix "d". Closed loop experiments were performed to investigate the time taken to raise the temperature of a given volume of fluid from one temperature to another with continual recirculation around the circuit. A requirement of these experiments, derived from the clinical situation, was that the temperature of the Peltier elements should be no more than 12° C. above the temperature of the blood/water at any time. A fluid bag having a volume of approximately 1500 mL was used to represent the blood volume of a neonatal patient.

FIG. 16(a) shows an elevated front view of a modified integrated perfusion device 100e. The modified integrated perfusion device 100e of FIG. 16a is generally similar to the device 100c of FIG. 14, like part being denoted by like numerals, supplemented by the suffix "e". However, the device 100e of FIG. 16a is a flat, channelled aluminium device. In this embodiment, the device 100e functions as a heat control unit. The device 100e comprises an upper portion 175e and a lower portion 155e. 8 Peltier elements 142e provided on the upper portion 175e of the device 100e. In this embodiment, the upper portion 175e and a lower portion 155e are connected by screws. In this embodiment, the device 100e is positioned in a substantially horizontal configuration. In other embodiments, the device 100e may be positioned in a variety of configurations, such as substantially vertically, or obliquely, without affecting the operation and performance of the device 100e.

FIG. 16(b) shows a cross-sectional view of the lower portion 155e of the device 100e along a line (i)-(i). As shown on FIG. 16(b), the fluid flow path is in the form of a conduit 156e extending within the lower portion 155e between inlet 101e and outlet 102e. The fluid conduit 156e is in contact or in proximity with the Peltier elements 142e provided on the upper portion 175e. The fluid path 156e is configured so as to maximise or provide high contact area between the fluid and the Peltier elements 142e, thereby improving thermal exchange. In this embodiment, the conduit 156e extends substantially lengthwise within the device 100e. In other embodiments, the conduit 156e may have different configurations, such as widthwise, oblique, or coil-like, while still providing large contact area for optimised thermal exchange with the Peltier elements 142e.

The results of the experiments carried out are shown in FIGS. 17(a) to 20.

FIGS. 17(a) to 17(g) show various measurements made using the device 100b of FIGS. 13(a) to 13(c).

Figure 17A:
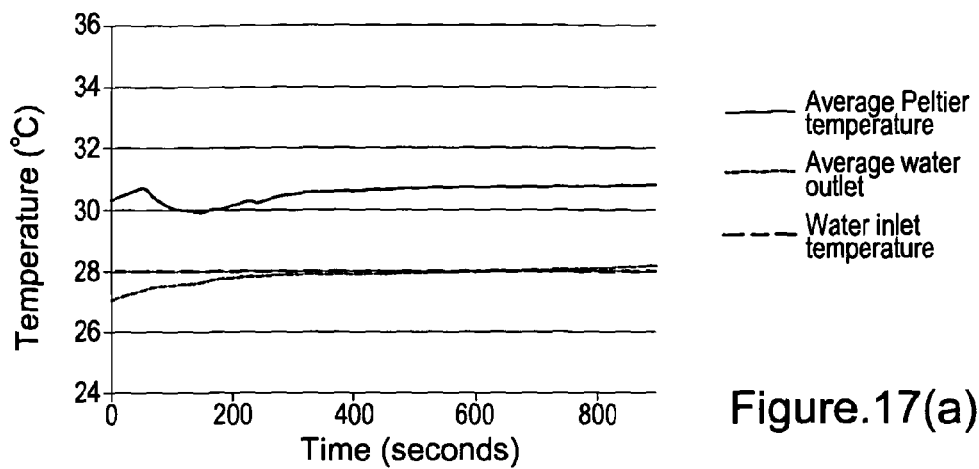
FIGS. 17(a) to 17(g) results of experiments made using the device of FIG. 13(a)

FIG. 17(a) shows the temperature of the water outlet and Peltier elements over time. For this experiment the device was equipped with 4 Peltier elements 142b connected in parallel. The Peltier control temperature was set at 32° C. using a TE Tech temperature controller, and the water inlet temperature was set at 28° C. The water flow rate was 400 mL/min. It can be seen that the water outlet temperature was initially lower than the water inlet temperature, due to heat loss through the device. However, after the initial activation period of the Peltier elements, it can been seen that the device was effective at maintaining the water outlet at the same temperature as the water inlet by controlling the temperature of the Peltier elements.

Figure 17B:
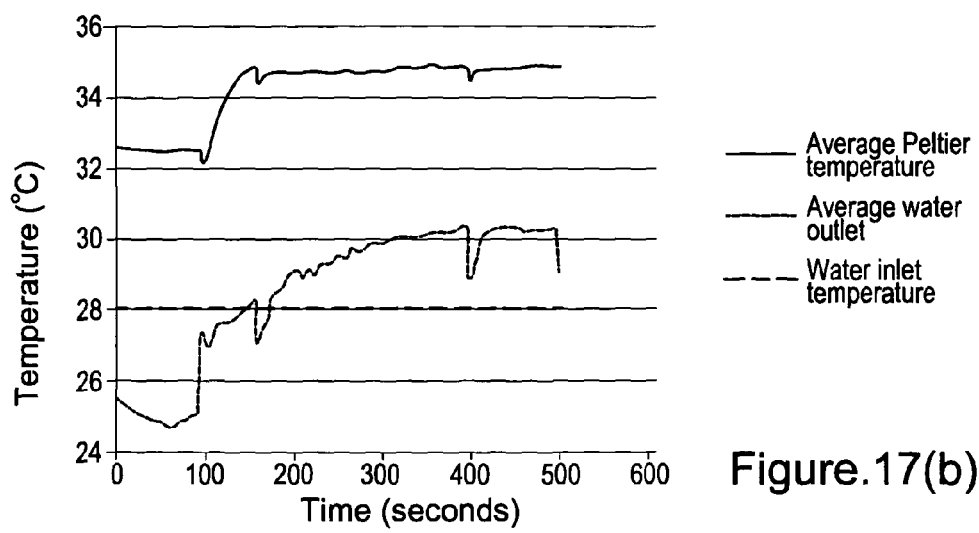

FIG. 17(b) shows the temperature of the water outlet and Peltier elements over time. For this experiment the device was equipped with 4 Peltier elements 142b connected in series. The other parameters were identical to the experiment shown in FIG. 17(a). The graph suggests that the average temperature of the Peltier elements needs to be set to a higher temperature when the Peltier elements are in series, as compared to Peltier elements arranged in parallel.

Figure 17C:
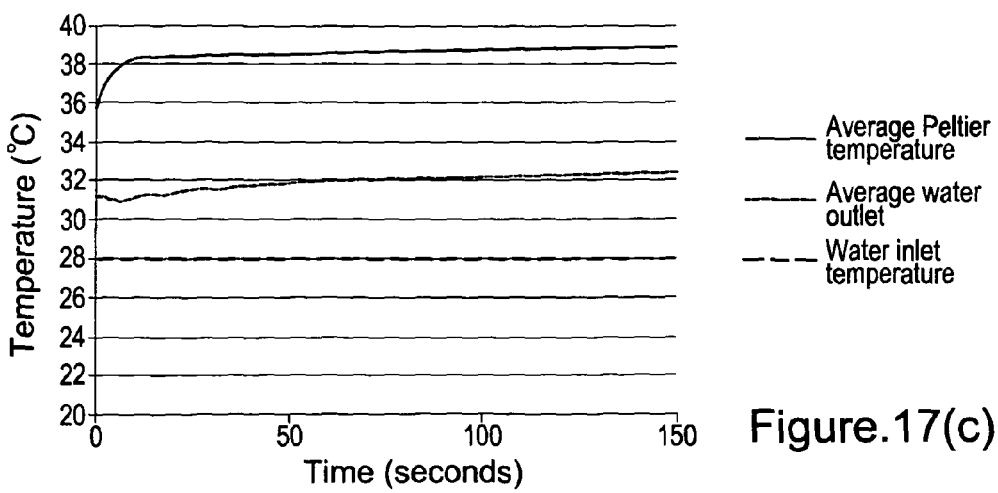
Figure 17D:
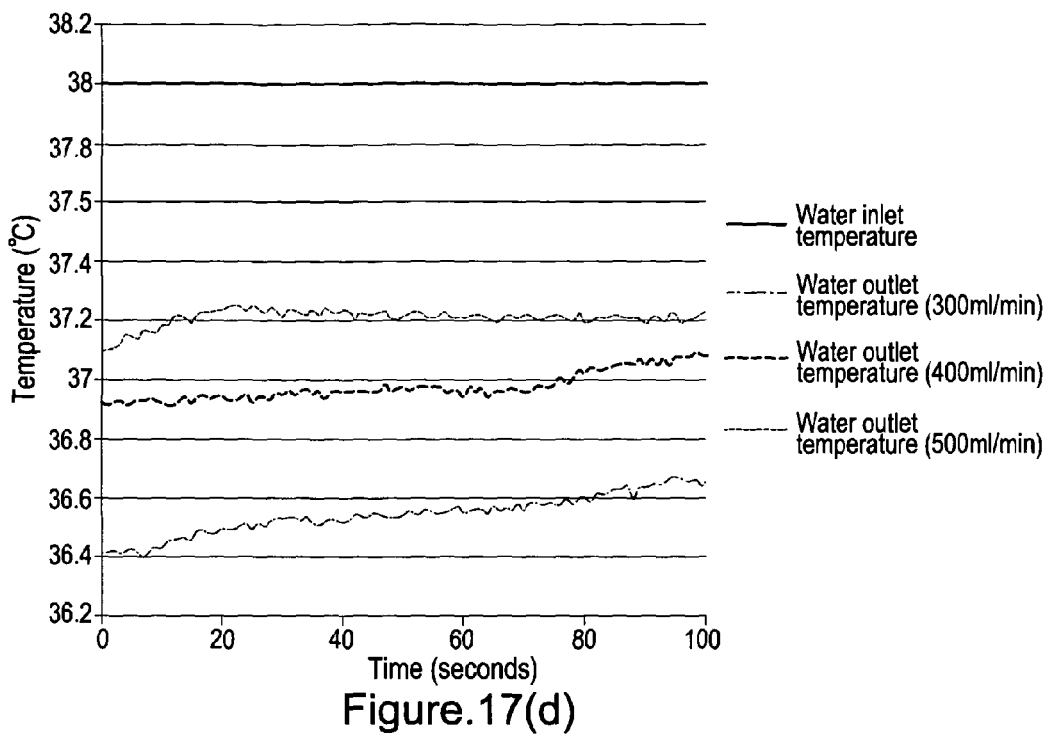
Figure 17E:
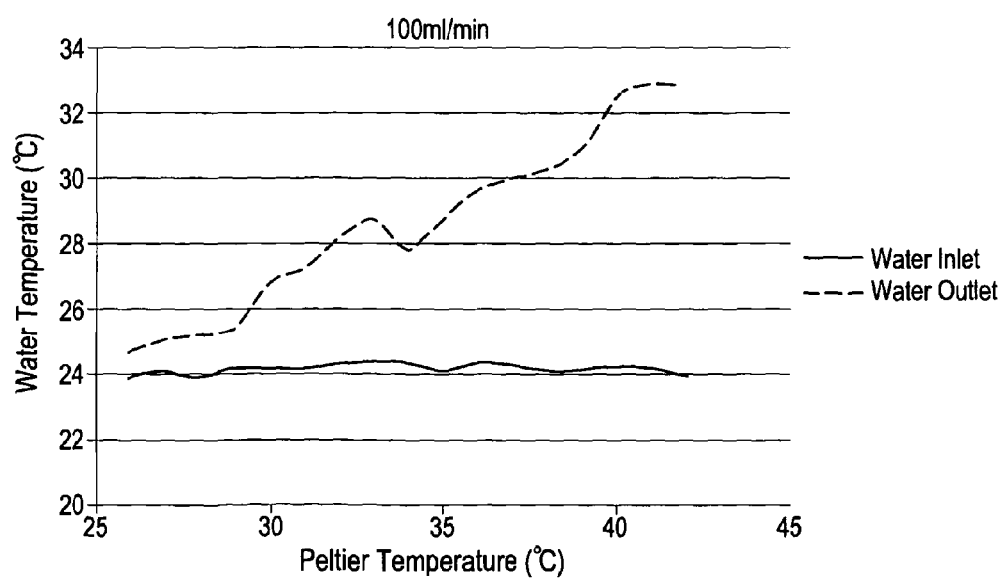
Figure 17F:
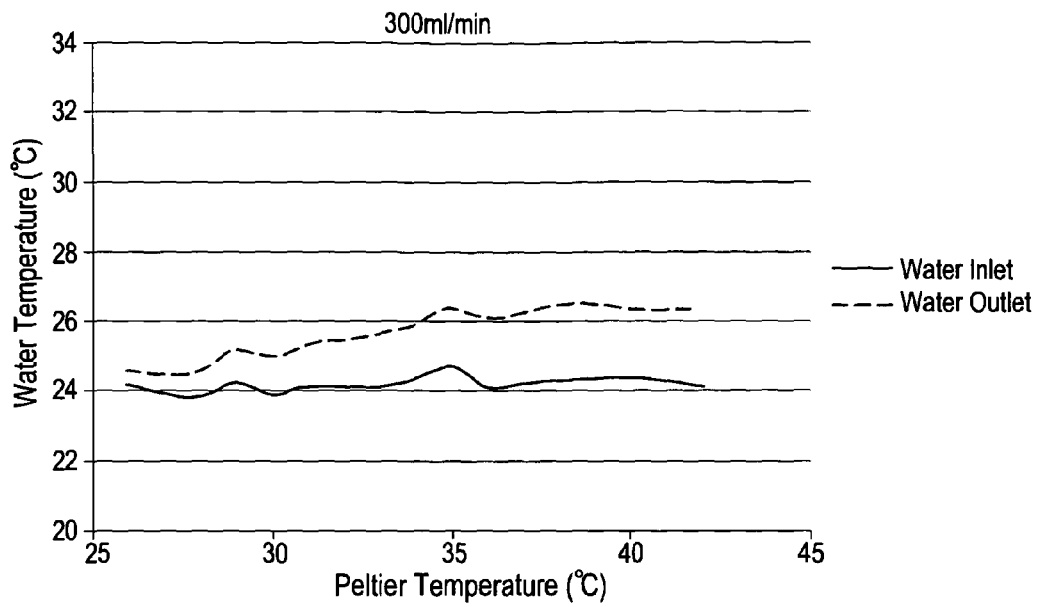
Figure 17G:
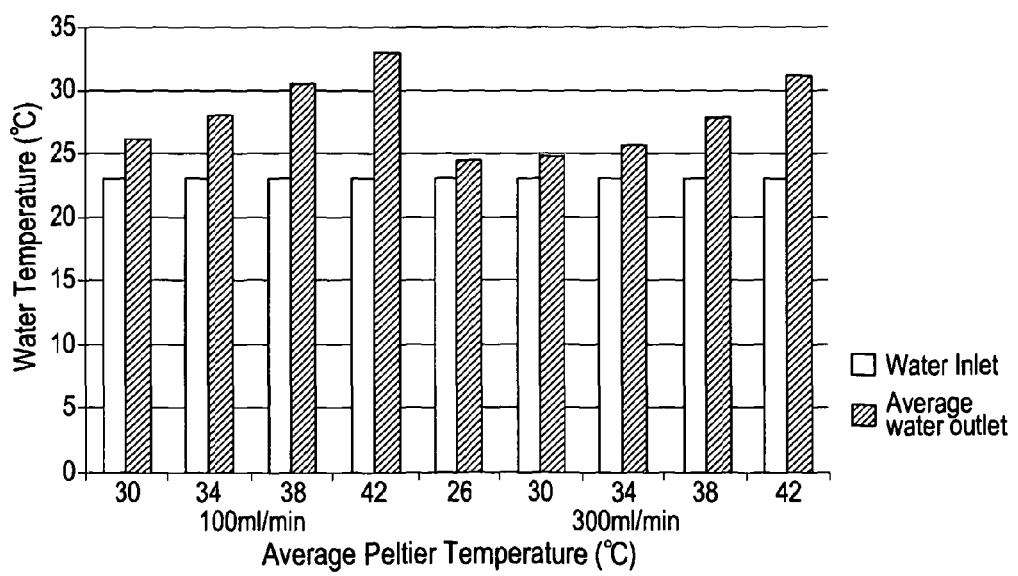
Figure 18A:
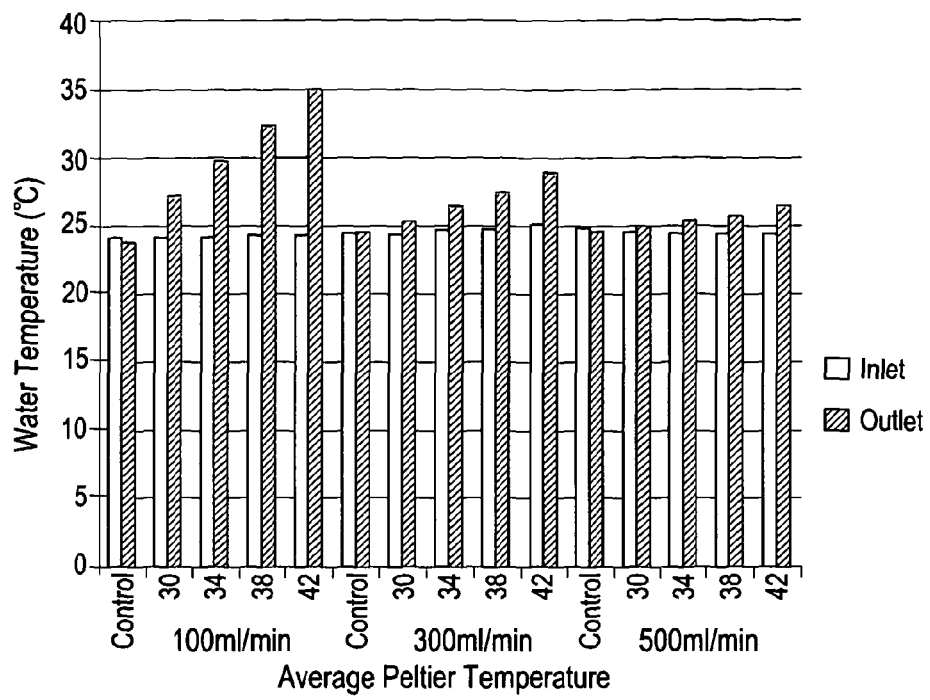
FIGS. 18(a) to 18(d) results of experiments made using the device of FIG. 14.
Figure 18B:
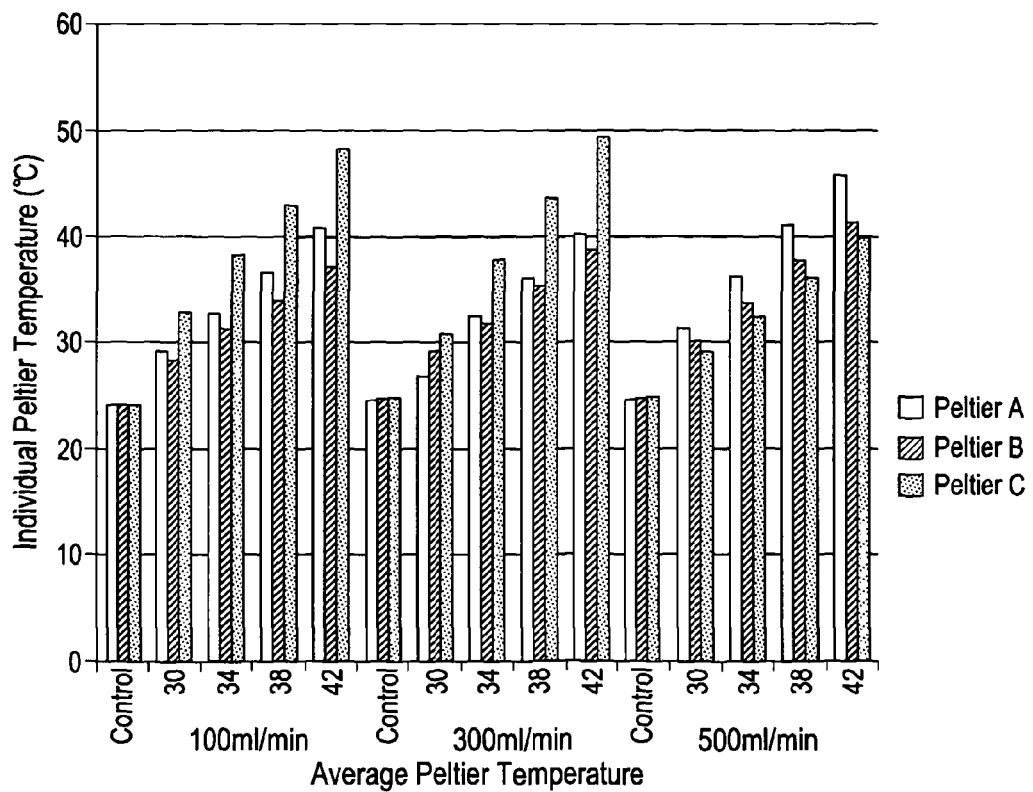
Figure 18C:
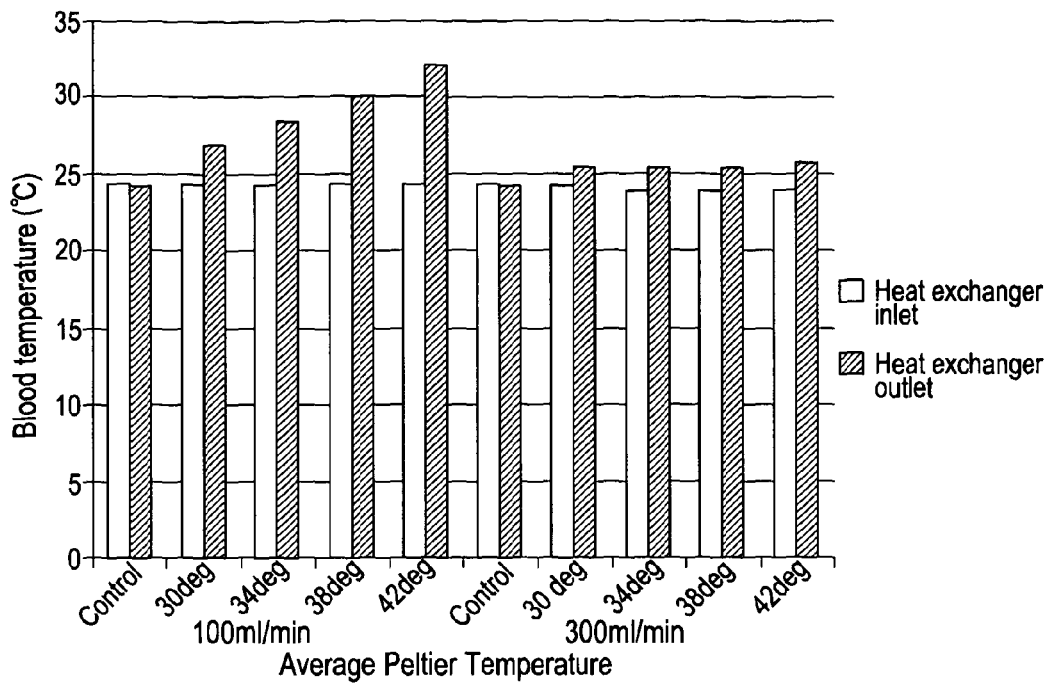
Figure 18D:
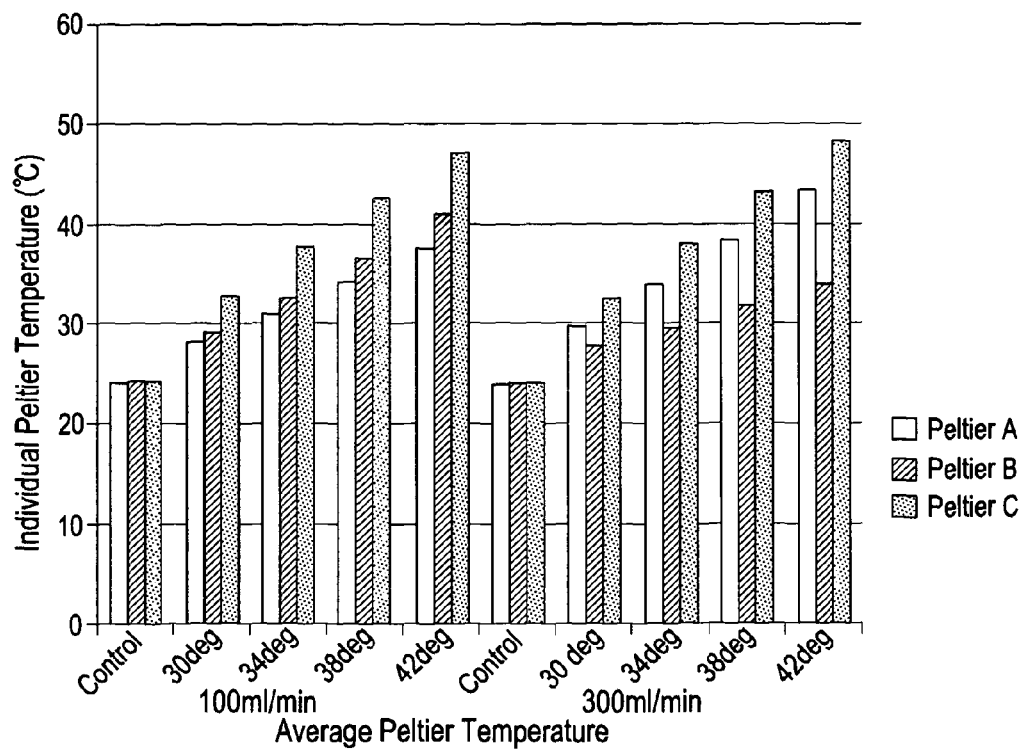

FIG. 17(c) shows the temperature of the water outlet, water inlet, and Peltier elements over time. For this experiment the device was equipped with 4 Peltier elements 142b connected in series. The Peltier control temperature was set to 38° C. using a TE Tech temperature controller, and the water inlet temperature was maintained at 28° C. The water flow rate was 400 mL/min. It can be seen that the device was effective at heating the water passing through the device 100*b*, and at maintaining the water outlet temperature substantially constant over time.

FIG. 17(*d*) shows the temperature of the water outlet and water inlet for three different flow rates: 300 mL/min, 400 mL/min and 500 mL/min. For this experiment the device 100*b* was equipped with 4 Peltier elements 142*b* connected in series. The Peltier control temperature was set to 42° C. using a TE Tech temperature controller, and the water inlet temperature was maintained at 38° C. It can be seen that for each flow rate the device was able to maintain water outlet temperature relative constant. However, it can be seen that the temperature of the water outlet varies depending on flow rate. This was expected, as the flow rate influences the amount of heat exchange possible with the Peltier elements, and also, in the case of a high water inlet temperature, the amount of heat loss through the device.

FIG. 17(*e*) shows the temperature of the water outlet and water inlet against the set temperature of the Peltier elements. For this experiment the device 100*b* was equipped with 8 Peltier elements 142*b* connected in parallel. The temperature of the Peltier elements was increased progressively. The water inlet temperature was maintained at 24° C. In the experiment the water flow rate was 100 mL/min. It can be seen that, as expected, the water outlet temperature increased as the temperature of the Peltier elements was increased.

FIG. 17(*f*) shows the temperature of the water outlet and water inlet against the set temperature of the Peltier elements, as per FIG. 17(*e*). However, in the experiment of FIG. 17(*f*), the water flow rate was 300 mL/min. As for FIG. 17(*e*), the water outlet temperature increased as the temperature of the Peltier elements was increased. However, when comparing FIGS. 17(*e*) and 17(*f*), it can be seen that increase in water outlet temperature through the device is less at higher flow rates. This was expected as the contact time for heat exchange with the Peltier elements through the device is reduced at higher flow rates.

FIG. 17(*g*) shows the temperature of the water outlet and water inlet for a range of set Peltier temperatures, both at a flow rate of 100 mL/min and 300 mL/min. The water inlet temperature was maintained at 23° C. In this experiment, the device 100*b* was equipped with 8 Peltier elements 142*b* individually controlled and each connected to its own power supply. Again, it can be seen that the water outlet temperature increased as the temperature of the Peltier elements was increased. Also, the increase in water outlet temperature through the device is less at higher flow rates.

FIGS. 18(*a*) and 18(*d*) show various measurements made using the device 100*c* of FIG. 14. In all experiments of FIGS. 18(*a*) to 18(*d*), the device 100*c* was equipped with 8 Peltier elements 142*c* connected in parallel. No temperature controller was used, and the temperature of 3 Peltier elements 142*c* was measured and averaged. The voltage was changed to control Peltier temperature.

FIG. 18(*a*) shows the temperature of the water outlet and water inlet for a range of set Peltier temperatures, at a flow rate of 100 mL/min, 300 mL/min and 500 mL/min. The water inlet temperature was maintained at 24° C. It can be seen that the water outlet temperature increased as the temperature of the Peltier elements was increased. Also, the increase in water outlet temperature through the device is less at higher flow rates.

FIG. 18(*b*) shows the temperature of the three Peltier elements whose temperatures were used to control the complete Peltier element array, at a flow rate of 100 mL/min, 300 mL/min and 500 mL/min. FIG. 18(*b*) shows that Peltier elements are very dynamic structures and that the precise temperature of each Peltier element is difficult to control. This suggest that temperature control of the device 100*c* would be best achieved by using a number of Peltier elements to help achieve the desired temperature on average.

FIGS. 18(*c*) and 18(*d*) are similar experiments to those of FIGS. 18(*c*) and 18(*d*), using porcine blood instead of water, at a flow rate of 100 mL/min and 300 mL/min.

FIGS. 18(*c*) and 18(*d*) show that the same conclusions as reached in FIGS. 18(*a*) and 18(*b*) can be made when using blood instead of water. In particular, FIGS. 18(*c*) and 18(*d*) show that the device 100*c* is effective at increasing the blood outlet temperature of blood passing through the device.

Figure 19A:
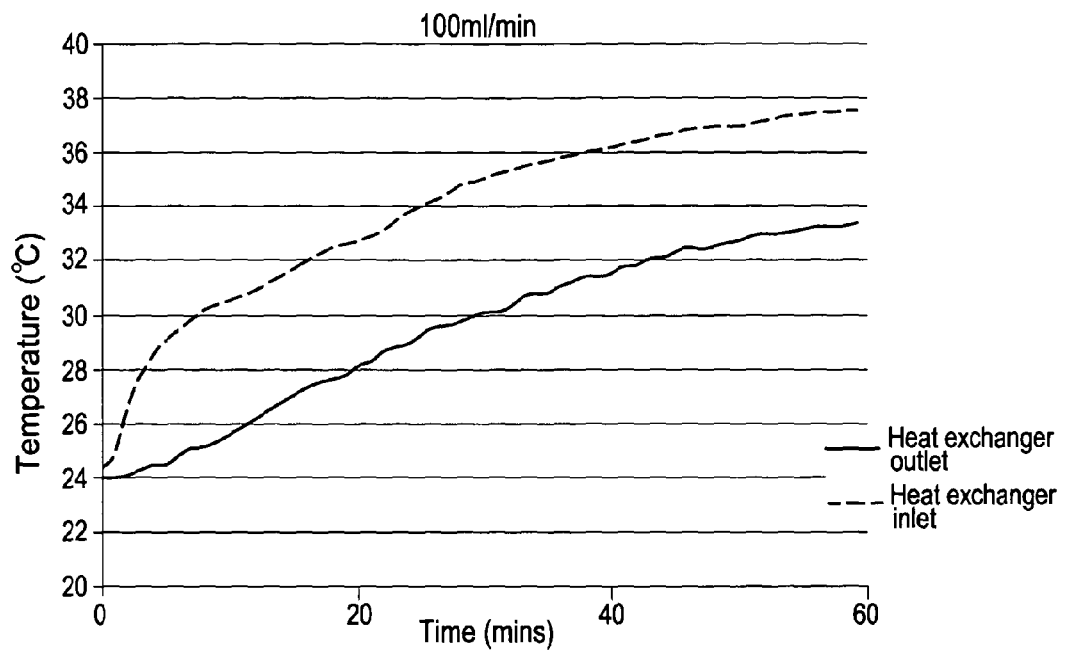
FIGS. 19(a) and 19(b) results of experiments made using the device of FIG. 15.
Figure 19B:
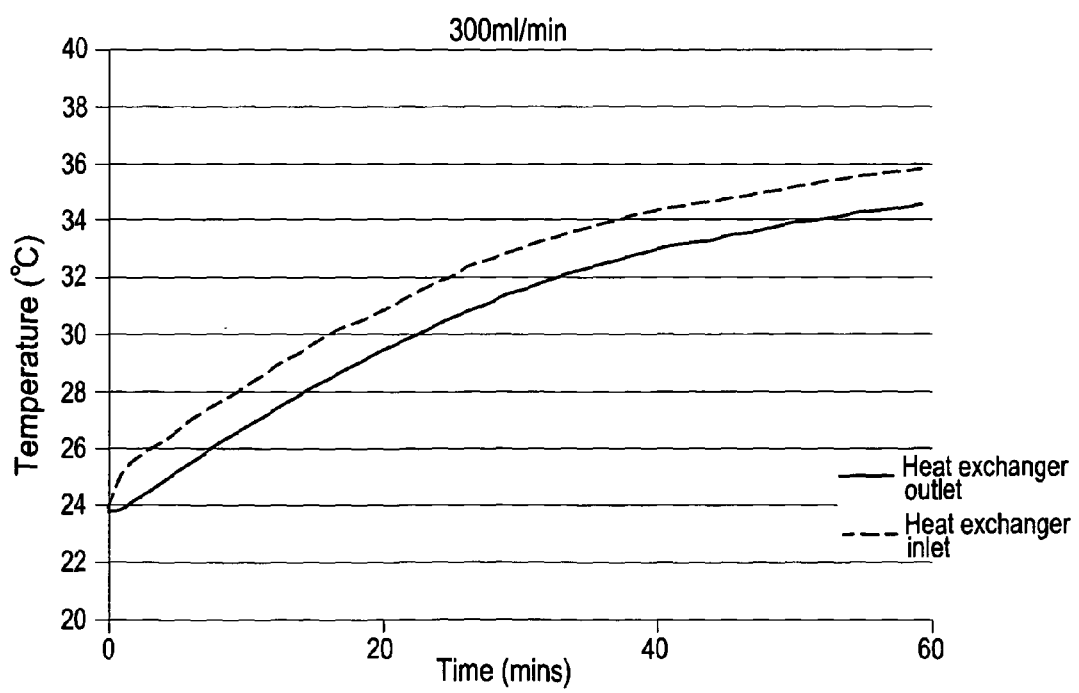

FIGS. 19(*a*) and 19(*b*) show various measurements made using the device 100*d* of FIG. 15. The closed circuit device 100*d* was equipped with 8 Peltier elements 142*d* connected in parallel, 60V, 20 A power supply. The temperature of the Peltier elements was kept at 12° C. above water inlet temperature. The graphs show the increase in water outlet temperature versus time, to increase bag temperature from 24° C. to 37° C., at water flow rate of 100 mL/min (FIG. 19(*a*)), and at 300 mL/min (FIG. 19(*b*)).

The graphs show that the device 100*d* was effective at increasing water temperature, both at 100 and at 300 mL/min flow rates.

Figure 20:
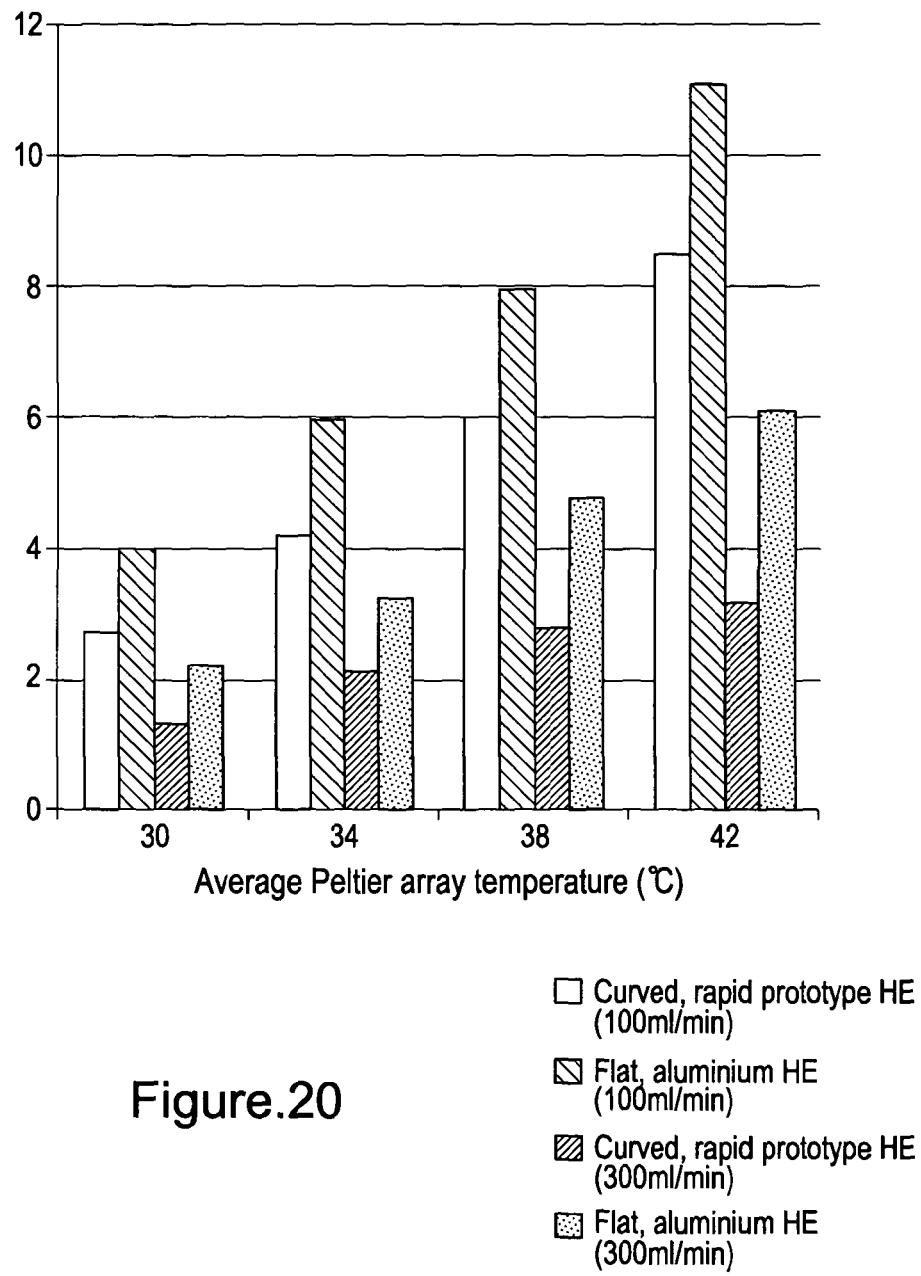
FIG. 20 results of experiments made using the device of FIG. 16.

FIG. 20 shows a comparison of the performance of the devices 100*c*,100*e* of FIGS. 14 and 16. For the experiment involving the flat aluminium device 100*e* of FIG. 16, 8 Peltier elements were connected in parallel. No temperature controller was used, the temperature of 3 Peltier elements was measured and averaged, and the voltage changed to control Peltier temperature. The water inlet temperature was maintained at 24° C.

FIG. 20 shows that whilst both designs are effective at increasing water temperature, the flat design 100*e* appears more efficient due to the tortuous fluid path conduit 156*e* which provides increased thermal exchange with the Peltier elements 142*e*.

It will be appreciated that the embodiments of the invention hereinbefore described are given by way of example only and are not meant to limit the scope thereof in any way.

The invention claimed is:

1. An integrated perfusion device comprising:
   a blood pump for circulating blood through the device;
   a blood oxygenator for oxygenating blood; and
   at least one heat control unit capable of controlling and/or regulating blood temperature within the device, wherein the at least one heat control unit comprises a plurality of solid state heating and/or cooling sources,
   wherein:
   the at least one heat control unit comprises at least one heat exchanger for regulating and controlling blood temperature;
   the heat control unit further comprises a temperature control unit;
   the temperature control unit is configured to independently monitor and control the temperature of each of the plurality of solid state heating and/or cooling sources; and
   the temperature control unit comprises a shut-down or override function configured for at least one of shutting down or overriding independently each of the plurality of solid state heating and/or cooling sources.

2. An integrated perfusion device according to claim 1, wherein the plurality of solid state heating and/or cooling sources is capable of both heating and cooling.

3. An integrated perfusion device according to claim 1, wherein the plurality of solid state heating and/or cooling sources comprises a plurality of solid-state thermoelectric heat pumps or Peltier devices.

4. An integrated perfusion device according to claim 1, wherein:
the at least one heat exchanger comprises a first side or portion at least one of in contact with, in proximity with, and associated with the blood to be heated and/or cooled, such that the at least one heat exchanger does not extend into the blood flow path.

5. An integrated perfusion device according to claim 4, wherein the at least one heat exchanger comprises a second side or portion at least one of in contact with, in proximity with, and associated with one or more of the plurality of solid state heating and/or cooling sources.

6. An integrated perfusion device according to claim 1, further comprising a heat exchange interface for regulating and controlling blood temperature, wherein the heat exchange interface comprises at least part of the blood oxygenator.

7. An integrated perfusion device according to claim 6, wherein the heat exchange interface comprises a gas exchange bundle of the blood oxygenator.

8. An integrated perfusion device according to claim 6, wherein blood temperature control is carried out by controlling the temperature of a ventilating gas supplied to the blood oxygenator.

9. A perfusion assembly comprising an integrated perfusion device according to claim 8, wherein the assembly further comprises a gas heat exchanger for controlling the temperature of the ventilating gas.

10. An integrated perfusion device according to claim 1, wherein the blood pump comprises a vortex pump.

11. An integrated perfusion device according to claim 1, wherein the device defines a blood flow path and comprises at least one blood inlet, at least one blood outlet, at least one ventilating gas inlet for supply to the blood oxygenator, and at least one ventilating gas outlet for release of exhausted gas from the blood oxygenator.

12. An integrated perfusion device according to claim 1, wherein the integrated perfusion device is a single use integrated perfusion device.

13. A perfusion assembly comprising a device according to claim 1.

14. A perfusion assembly according to claim 13, comprising an ECMO assembly, a CPB assembly, an isolated limb perfusion assembly, a limb preservation assembly, an isolated organ perfusion assembly, a neurosurgery assembly, a liver surgery assembly, a pancreatic surgery assembly, or a vascular assembly.

15. A method of performing perfusion on a patient, limb or organ, comprising using a perfusion device according to claim 1.

* * * * *